(12) United States Patent
Zhang et al.

(10) Patent No.: US 7,105,702 B2
(45) Date of Patent: Sep. 12, 2006

(54) P-CHIRAL PHOSPHOLANES AND PHOSPHOCYCLIC COMPOUNDS AND THEIR USE IN ASYMMETRIC CATALYTIC REACTIONS

(75) Inventors: Xumu Zhang, State College, PA (US); Wenjun Tang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 10/291,232

(22) Filed: Nov. 8, 2002

(65) Prior Publication Data
US 2003/0144137 A1   Jul. 31, 2003

Related U.S. Application Data

(60) Provisional application No. 60/336,939, filed on Nov. 9, 2001.

(51) Int. Cl.
C07F 9/02 (2006.01)
(52) U.S. Cl. .............................. 568/8; 568/12; 568/70; 568/73; 564/114
(58) Field of Classification Search ................ 568/8, 568/12, 70, 73; 558/70, 73; 564/114
See application file for complete search history.

(56) References Cited

U.S. PATENT DOCUMENTS

| | | | | |
|---|---|---|---|---|
| 5,149,878 | A * | 9/1992 | Robertson et al. | 568/12 |
| 5,322,956 | A * | 6/1994 | Burk | 556/22 |
| 5,936,109 | A * | 8/1999 | Berens | 556/14 |
| 6,043,396 | A * | 3/2000 | Sturmer et al. | 568/12 |
| 6,492,544 | B1 * | 12/2002 | Krimmer et al. | 560/170 |
| 6,545,183 | B1 * | 4/2003 | Berens | 568/12 |
| 6,605,745 | B1 * | 8/2003 | Hoge et al. | 568/12 |
| 2002/0087017 | A1 | 7/2002 | Hoge, II et al. | 556/18 |
| 2004/0229846 | A1 * | 11/2004 | Zhang et al. | 514/80 |

OTHER PUBLICATIONS

CA:138:55724 abs of Organic Letters by Tang et al 4(23) pp. 4159-4161 2002.*
CA:17:311163 abs of Angewandte Chemie International Edition by Tang et al 41(9) pp. 1612-1614 2002.*
CA:103:215527 abs of Inorganic Chemistry by Mercier et al 24(24) pp. 4141-4149 1985.*
He et al., Optical Resolution, Configurational Stability, and Coordination Chemistry of the P-Chiral Heterocyclic Diphosphine 1,1'-Diphenyl-3,3',4,4'-tetramethyl-2'2-diphosphole-3'3'-diene, Organometallics, (1999), 18 (20), 4027-4031.*
Bienewald et al., A New Ligand Containing a Unique Combination of Backbone and P-Centered Chirality: Synthesis, Resolution and Asymmetric Catalysis Using a Chiral Enatiopure 2, 2'-Biphospholene, Tetrahedron: Asymmetry, 10 (1999), 4701-4707.*

Zublocka et al., Inverse Hydrozirconation: A Regio- and Diasterospecific Path to New Diphosphines, Angewandte Chemie, 1993, 105 (12), 1846-8.*
Database CAPLUS on STN, Chemical abstracts CA:120:245287, Zublocka et al.—"Inverse hydrozirconation: a regio- and diastereospecific path to new diphosphines", Angew Chem. Int. Ed. 1993, 32(12) pp. 1735-1737.
Database CAPLUS on STN, Chemical abstracts CA:123:228297, Zablocka et al. —"Unprecedented inversion of configuration at carbon in the electrophilic cleavage or the carbon-zirbondium (IV) bond", Journ. Of the American Chem. Soc., 1995, 117(31) pp. 8083-8089.
Database CAPLLUS on STN, Chemical abstracts CA:123:144020, Bianchini et al. —"N new P-chiral aminophosphine ligand containing a 2, 2'-coupled pyrrolidine-phospholane ring system. Synethsis and coordination properties with rhodium (I) and iridium (I) fragments", Journ. Of the American Chem. Soc., Chemical Communications, 1995, (8) pp. 833-834.
Database CAPLUS on STN, Chemical abstracts CA:119:72317, Von Matt et al.—"Chiral ( phoshinoaryl) dihydrooxazoles as ligands in asymmetric catalysis: palladium-catalyzed allylic substitution", Angewandte Chemie Int. Ed Engl. 1993, 32(4) pp. 566-568.
Database CAPLUS on STN, Chemical abstracts CA:124:76831, Field et al.—"Synthesis of New Bidentate Phosphine Ligands Containing Saturated Phosphorus Heterocycles", Inorganic Chemistry, 1996, 35(9) pp. 2546-2548.
Ojima, "Catalytic asymmetric synthesis," VCH, New York, 1993.
Noyori, "Asymmetric catalysis in organic synthesis," John Wiley & Sons, Inc., New York, 1994.
Knowles, "Asymmetric Hydrogenation," Ass. Chem. Res., 16, 106-112, 1983.
Krapcho et al., "2-Carbethoxycyclooctanone," J. Org. Synth., 5, 198-201, 1973.
Yamago et al. "Tertiary phosphines and P-chiral phosphinites bearing a fullerene substituent," J. Chem. Soc., Chem. Comm., 2093-2094, 1994.

(Continued)

Primary Examiner—Johann Richter
Assistant Examiner—Chukwuma Nwaonicha
(74) Attorney, Agent, or Firm—Ohlandt, Greeley, Ruggiero & Perle, L.L.P.

(57) ABSTRACT

Chiral ligands and metal complexes based on such chiral ligands useful in asymmetric catalysis are disclosed. The metal complexes according to the present invention are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution and [m+n] cycloaddition. Processes for the preparation of the ligands are also described.

7 Claims, No Drawings

OTHER PUBLICATIONS

Togni, "Planar-chiral ferrocenes: synthetic methods and applications." Angew. Chem. Int. Ed. Engl., 35 No. 13/14, 1475-1477, 1996.

McKinstry et al. "An efficient procedure for the synthesis of elecron rich bisphosphines containing homochiral Backbones." Tetrahedron Letters, vol. 35, No. 50, 9319-9322, 1994.

Zhu et al. "Highly efficient asymmetric synthesis of β-amino acid derivatives via rhodium-catalyzed hydrogenation of β-(acylamino)acrylates," J. Org. Chem., 64, 6907-6910, 1999.

Gridnev et al. "Asymmetricd hydrogenation catalyzed by (S, S)-R-BisP-Rh and (R, R)-R-MiniPHOS Complexes: Scope, Limitations, and Mechanism," Adv. Synth. Catal., 343, No. 1, 118-136, 2001.

Ohashi et al., "Highly enantioselective hydrogenation of a-dehydroamino acids by rhodium complexes with new unstmmetric p-chirogenic bisphosphine ligands," Org. Lett., vol. 3, No. 3, 373-375, 2001.

Yamanoi et al. "Methylene-bridged p-chiral diphosphines in highly enantioselective reactions." J. Org. Chem., 64, 2988-2989, 1999.

Blankenstein et al. "A new class of modular phosphinite-oxazoline ligands: Ir-catalyzed enantioselective hydrogenation of alkenes." Angew. Chem. Int. Ed., 40, No. 23, 4445-4447, 2001.

Lightfoot et al. "Enantioselective hydrogenation of olefins with Iridium-Phosphanodihyrooxazole catalysts." Angew. Chem. Int. Ed., 37, No. 20, 2897-2899, 1998.

Hou et al. "New, optically active phosphine oxazoline (JM-Phos) ligands: Syntheses and applications in allylation Reactions." J. Org. Chem., 66, 206-215, 2001.

Zhou et al. Highly effective chiral ortho-substituted BINAPO ligands (o-BINAPO): applications in Ru-catalyzed asymmetric hydrogenations of β-aryl-substituted β-(acylamino)acrylates and β-keto esters, J. Am. Chem. Soc. 124, 4952-53, 2002.

Littke et al. "A versatile catalyst for heck reactions of aryl chlorides and aryl bromides under mild conditions." J. Am. Chem. Soc., 123, 6989-7000, 2001.

Powell et al. "Chiral imidazolylidine ligands for asymmetric hydrogenation of aryl alkenes." J. Am. Chem. Soc., 123 8878-8879, 2001.

Gridney et al. "Asymmetric hydrogenation of enamides with Rh-BisP and Rh-miniPHOS catalysts. Scope, Limitations, and Mechanism." J. Am. Chem. Soc., 123, 5268-5276, 2001.

Zon et al. "The stereospecific desulfurization of acyclic phosphine sulfides with hexachlorodisilane and the alkaline Hydrolysis of monoalkoxy- and monoalkylmercaptophosphonium salts." J. Am. Chem. Soc., 91:25, 7023-7027, 1969.

Imamoto et al. Synthesis and reactions of phosphine-boranes. Synthesis of new bidentate ligands Homochiral phosphine centers via optically pure phosphine-boranes, J. Am. Chem. Soc., 112, 5244-5252, 1990.

Maryanoff et al. A one-step synthesis of optically pure 1, 2-ethano bis sulfoxides and phosphine oxidesvia the Copper-promoted oxidative dimerization of chiral sulfinyl and phosphinyl carbanions, J. Am. Chem. Soc., 95:17, 5839-40, 1973.

Muci et al. "Enantioselective deprotonation as a vehicle for the asymmetric synthesis of C2-symmetric p-chiral Diphosphines." J. Am. Chem. Soc., 117, 9075-9076, 1995.

Corey et al. "A new and highly enantioselective synthetic route to p-chiral phosphines and diphosphines." J. Am. Chem. Soc., 115, 11000-11001, 1993.

Vineyard et al. "Asymmetric hydrogenation. Rhodium chiral bisphosphine catalyst." J. Am. Chem. Soc., 99:18, 3946-3952, 1977.

Noyori et al. "BINAP: An efficient chiral element for asymmetric catalysis." Acc. Chem. Res., 23, No. 10, 345-250, 1990.

\* cited by examiner

P-CHIRAL PHOSPHOLANES AND PHOSPHOCYCLIC COMPOUNDS AND THEIR USE IN ASYMMETRIC CATALYTIC REACTIONS

This application claims priority from U.S. Provisional Application Ser. No. 60/336,939, filed Nov. 9, 2001.

STATEMENT OF GOVERNMENT RIGHTS

This invention was made with support from the Government under Grant No. 1R01 GM58832. The Government has certain rights in the invention.

BACKGROUND OF THE INVENTION

1. Field of the Invention

The present invention relates to novel chiral ligands derived from P-chiral phospholanes and P-chiral phosphocyclic compounds and catalysts for applications in asymmetric catalysis. More particularly, the present invention relates to transition metal complexes of these chiral phosphine ligands, which are useful as catalysts in asymmetric reactions, such as, hydrogenation, hydride transfer, hydrocarboxylation, hydrosilylation, hydroboration, hydrovinylation, hydroformylation, allylic alkylation, olefin metathesis, isomerization, cyclopropanation, Diels-Alder reaction, Heck reaction, Aldol reaction, Michael addition, epoxidation, kinetic resolution and [m+n] cycloaddition.

2. Description of the Prior Art

Molecular chirality plays an important role in science and technology. The biological activities of many pharmaceuticals, fragrances, food additives and agrochemicals are often associated with their absolute molecular configuration. A growing demand in pharmaceutical and fine chemical industries is to develop cost-effective processes for the manufacture of single-enantiomeric products. To meet this challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is perhaps the most efficient because a small amount of a chiral catalyst can be used to produce a large quantity of a chiral target molecule [Book, Ojima, I., Ed. *Catalytic Asymmetric Synthesis,* VCH, New York, 1993 and Noyori, R. *Asymmetric Catalysis In Organic Synthesis,* John Wiley & Sons, Inc., New York, 1994].

Asymmetric hydrogenation accounts for major part of all asymmetric synthesis on a commercial scale. Some dramatic examples of industrial applications of asymmetric synthesis include Monsanto's L-DOPA synthesis (asymmetric hydrogenation of a dehydroamino acid, 94% ee, 20,000 turnovers with a Rh-DIPAMP complex) [Knowles, W. S. *Acc. Chem. Res.* 1983, 16, 106], Takasago's L-menthol synthesis (asymmetric isomerization, 98% ee, 300,000 turnovers with a Rh-BINAP complex) [Noyori, R.; Takaya, H. *Acc. Chem. Res.* 1990, 23, 345] and Norvatis' (S)-Metolachlor synthesis (asymmetric hydrogenation of an imine, 80% ee, 1,000,000 turnovers with an Ir-ferrocenyl phosphine complex) [Spindler, F.; Pugin, B.; Jalett, H.-P., Buser, H.-P.; Pittelkow, U.; Blaser, H,-U., Altanta, 1996; Chem. Ind. (Dekker), 1996, 63 and Tongni, *A. Angew. Chem. Int. Ed. Engl.* 1996, 356, 14575].

Invention of chiral ligands for transition metal-catalyzed reactions plays a critical role in asymmetric catalysis. Not only the enantioselectivity depends on the framework of chiral ligands, reactivities can often be altered by changing the steric and electronic structure of the ligands.

Since small changes in the ligand can influence the (delta)(delta)G of the rate-determining step, it is very hard to predict which ligand can be effective for any particular reaction or substrate. Accordingly, discovery of new chiral ligands sets the foundation of highly enantioselective transition metal-catalyzed reactions.

In recent years, a large number of chiral ligands have been developed for use in asymmetric catalysis reactions. Despite this, only few chiral ligands have been found to be suitable for use in industry for the production of chiral molecules that require high selectivity.

One of the earliest P-chiral phosphine ligands is DIPAMP, which was developed by Knowles, *J. Am. Chem. Soc.,* 99, 5946 (1977). The Rh(I)-DIPAMP complex has been used in the synthesis of L-DOPA.

There are continuing efforts from many groups to develop strategies for making P-chiral ligands for asymmetric catalysis, including, for example, the following: I. Ojima, Ed., Catalytic Asymmetric Synthesis, $2^{nd}$ ed., VCH publishers, Wheinheim, 2000. Juge and Genet, *Tetrahedron Lett.,* 30, 6357 (1989), who have developed a method for making P-chiral phosphines. E. J. Corey, *J. Am. Chem. Soc.,* 115, 11000 (1993), who has developed a method for preparing P-chiral phosphines and diphosphines. An enantioselective deprotonation as a method for the synthesis of P-chiral phosphines has been applied by Evans, *J. Am. Chem. Soc.,* 117, 9075 (1995). Typically, phosphine-borane, phosphine sulfides have been used. Enantioselective deprotonation of these compounds and Cu-mediated coupling reactions can produce a number of diphosphines. A Cu-mediated coupling reaction was reported by Mislow, *J. Am. Chem. Soc.,* 95, 5839 (1973). Formation of phosphine-borane and removal of borane have been reported by Imamoto, *J. Am. Chem. Soc.,* 112, 5244 (1990), Yamago, *J. Chem. Soc., Chem. Commun.,* 2093 (1994) and Livinghouse, *Tetrahedron Lett.,* 35, 9319 (1994). Desulfurization of phosphine sulfides is reported by Mislow, *J. Am. Chem., Soc.,* 91, 7023 (1969). More recently, Imamoto has successfully used these strategies to make a number of P-chiral phosphines such as BisP*, *J. Am. Chem. Soc.,* 123, 5268 (2001), MiniPhos, *J. Org. Chem.,* 64, 2988 (1999) and other mixed P-chiral ligands, *Org. Lett.,* 3, 373 (2001).

These ligands have been used effectively in many asymmetric reactions, especially in asymmetric hydrogenation reactions, such as those described in Adv. Synth. Catal., 343, 118 (2001).

Some of these ligands are depicted below:

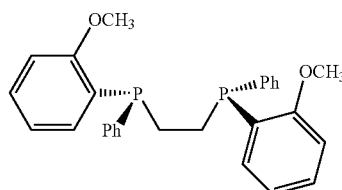

DIP AMP
Knowles

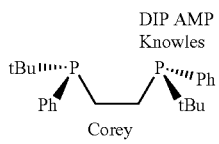

Corey

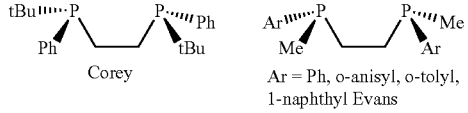

Ar = Ph, o-anisyl, o-tolyl, 1-naphthyl Evans

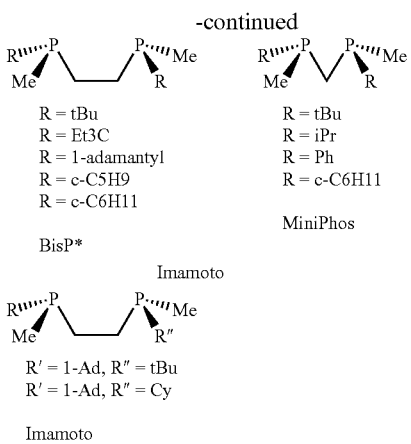

R = tBu
R = Et3C
R = 1-adamantyl
R = c-C5H9
R = c-C6H11

BisP*

R = tBu
R = iPr
R = Ph
R = c-C6H11

MiniPhos

Imamoto

R' = 1-Ad, R" = tBu
R' = 1-Ad, R" = Cy

Imamoto

Despite the wide variation in the substituted groups in the above ligands, the majority of these ligands are derivatives of the DIPAMP ligand. A possible drawback of these ligands is that ligands having a DIPAMP structure are conformationally flexible and, as a result, enantioselectivity is difficult to optimize.

In contrast to the ligands of the prior art, the present invention provides a phospholane and phosphocyclic structure to restrict the conformational flexibility such that a high enantioselectivity can be achieved in the transition metal catalysts prepared from these ligands.

Thus, from a stereochemical point of view, additional stereogenic centers (e.g. four or more stereogenic centers) are typically created to make the novel ligands of the present invention substantially more selective in asymmetric catalytic reactions than, for example, the DIPAMP and BisP* ligands, which have only two stereogenic centers.

SUMMARY OF THE INVENTION

The present invention provides a chiral ligand represented by the following formula or its enantiomer:

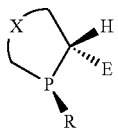

wherein X is a divalent group selected from $(CR^4R^5)_n$, $(CR^4R^5)_n$—Z—$(CR^4R^5)_n$ and group represented by the formula:

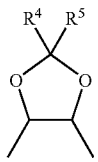

wherein each n is independently an integer from 1 to 6; wherein each $R^4$ and $R^5$ can independently be hydrogen, alkyl, aryl, substituted alkyl, substituted aryl, hetereoaryl, ferrocenyl, halogen, hydroxy, alkoxy, aryloxy, alkylthio, arylthio and amido; and wherein Z can be O, S, —COO—, —CO—, O—$(CR^4R^5)_n$—O, $CH_2$ $(C_6H_4)$, $CH_2$ (Ar), $CH_2$(hetereoaryl), alkenyl, $CH_2$(alkenyl), $C_5H_3N$, divalent aryl, 2,2'-divalent-1,1'-biphenyl, $SiR'_2$, PR' and $NR^6$ wherein each of R' and $R^6$ can independently be hydrogen, alkyl, substituted alkyl, aryl, substituted aryl, hydroxy, alkoxy, aryloxy, acyl and alkoxycarbonyl;

wherein R can be alkyl, aryl, substituted alkyl, substituted aryl, hetereoaryl, ferrocenyl, alkoxy and aryloxy;

wherein E can be $PR'_2$, PR'R", o-substituted pyridine, oxazoline, chiral oxazoline, $CH_2$(chiral oxazoline), CR'2 (chiral oxazoline), $CH_2PR'_2$, $CH_2$(o-substituted pyridine), $SiR'_3$, $CR'_2OH$ and a group represented by the formula:

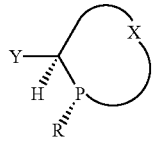

wherein Y can be $(CR^4R^5)_m$ and $(CR^4R^5)_m$—Z—$(CR^4R^5)_m$;

wherein each m is independently an integer from 0 to 3; wherein each $R^4$ and $R^5$ can independently be hydrogen, alkyl, aryl, substituted alkyl, substituted aryl, hetereoaryl, ferrocenyl, halogen, hydroxy, alkoxy, aryloxy, alkylthio, arylthio and amido; and wherein Z can be O, S, —CO—, —COO—, O—$(CR^4R^5)_n$—O, $CH_2$ $(C_6H_4)$, $CH_2$ (Ar), $CH_2$ (hetereoaryl), alkenyl, $CH_2$(alkenyl), $C_5H_3N$, divalent aryl, 2,2'-divalent-1,1'-biphenyl, $SiR'_2$, PR' and $NR^6$ wherein each of R' and $R^6$ can independently be hydrogen, alkyl, substituted alkyl, aryl, substituted aryl, hydroxy, alkoxy, aryloxy, acyl and alkoxycarbonyl.

More particularly, the present invention provides a chiral ligand represented by the formula and its enantiomer:

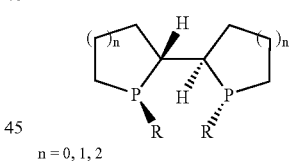

n = 0, 1, 2 wherein R can be alkyl, aryl, substituted alkyl, substituted aryl, hetereoaryl, ferrocenyl, alkoxy and aryloxy; and wherein n is from 0 to 2.

The present invention further provides a catalyst prepared by a process including:

contacting a transition metal salt, or a complex thereof, and a chiral ligand according to the present invention as described herein above.

The present invention still further provides a process for preparation of an asymmetric compound including:

contacting a substrate capable of forming an asymmetric product by an asymmetric reaction and a catalyst prepared by a process including: contacting a transition metal salt, or a complex thereof, and a chiral ligand according to the present invention as described herein above.

The present invention still further provides a process for preparing (1R, 1R', 2R, 2R')-1,1'-di-alkyl -[2,2']-diphospholanyl-1,1'-disulfide including the steps of:

asymmetrically deprotonating a 1-alkyl-phospholane-1-sulfide with n-butyllithium/(−)-sparteine in a solvent to produce an anion of the 1-alkyl-phospholane-1-sulfide; and contacting the anion of the 1-alkyl-phospholane-1-sulfide and CuCl$_2$ to oxidatively couple the anion of the 1-alkyl-phospholane-1-sulfide and produce a reaction mixture including the (1R, 1R', 2R, 2R')-1,1'-di-alkyl-[2,2']-diphospholanyl-1,1'-disulfide.

Further still, the present invention provides a process for preparing (1S, 1S', 2R, 2R')-1,1'-di-alkyl-[2,2']-diphospholanyl including the steps of:

asymmetrically deprotonating a 1-alkyl-phospholane-1-sulfide with n-butyllithium/(−)-sparteine in a solvent to produce an anion of the 1-alkyl-phospholane-1-sulfide;

contacting the anion of the 1-alkyl-phospholane-1-sulfide and CuCl$_2$ to oxidatively couple the anion of the 1-alkyl-phospholane-1-sulfide and produce a reaction mixture including (1R, 1R', 2R, 2R')-1,1'-di-alkyl-[2,2']-diphospholanyl-1,1'-disulfide;

recrystallizing the (1R, 1R', 2R, 2R')-1,1'-di-alkyl-[2,2']-diphospholanyl-1,1'-disulfide from the reaction mixture; and contacting the (1R, 1R', 2R, 2R')-1,1'-di-alkyl-[2,2']-diphospholanyl-1,1'-disulfide and hexachlorodisilane in a solvent to produce (1S, 1S', 2R, 2R')-1,1'-di-alkyl-[2,2']-diphospholanyl.

The presence of additional stereogenic centers (e.g. four or more stereogenic centers) in the novel ligands of the present invention makes them substantially more selective in asymmetric catalytic reactions than, for example, the DIPAMP and BisP* ligands, which have only two stereogenic centers.

DETAILED DESCRIPTION OF THE INVENTION

The present invention provides novel P-chiral phospholane and phosphocyclic compounds and described their use in asymmetric catalysis.

Introduction of cyclic structures can restrict the rotation of substituents adjacent to the phosphines and control of orientations of these groups around phosphine can lead effective chiral induction for asymmetric reactions. Metal complexes of these phosphines, and related none C$_2$ symmetric ligands are useful for many asymmetric reactions.

Tunability of ligand chiral environment is crucial for achieving high enantioselectivity. The steric and electronic structure of the conformationally rigid cyclic phosphines can be fine-tuned by variation of ring size and substituents.

Several new chiral phosphines are developed for asymmetric catalytic reactions. A variety of asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition were developed with these chiral ligands systems.

The ligands of the present invention can be a racemic mixture of enantiomers. Preferably, the ligand is a non-racemic mixture of enantiomers, and more preferably, the ligand is one of the enantiomers. Preferably, the ligand has an optical purity of at least 85% ee, and more preferably, the ligand has an optical purity of at least 95% ee.

Representative examples of chiral ligands of the current invention are shown below. A number of chiral ligands with desired structures according to the present invention can be made and used in the preparation of the catalysts described in the present invention.

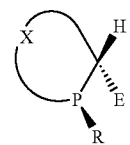

X=(CH$_2$)$_n$, n=1, 2, 3, 4, 5, 6. CH$_2$OCH$_2$, CH$_2$NHCH$_2$, CH$_2$CH(R')CH(R'), CH$_2$CH (OR')CH(OR'), CH$_2$CH(OH) CH(OH), CH$_2$CH(OCR'$_2$O)CH, CH$_2$CH(OalkylO)CH, CH$_2$CH(OCHR'O)CH, CH$_2$NR'CH$_2$, CH$_2$CH$_2$N R'CH$_2$, CH$_2$CH$_2$OCH$_2$, CH$_2$(C$_6$H$_4$), CH$_2$(Ar), CH$_2$(hetereoaryl), CH$_2$(alkenyl), alkyl, substituted alkyl, aryl, substituted aryl, CH$_2$(biaryl), CH$_2$(ferrocene).

R=alkyl, aryl, substituted alkyl, substituted aryl, hetereoaryl, ferrocene

E=PR'$_2$, PR'R'', o-substituted pyridine, oxazoline, chiral oxazoline, CH$_2$(chiral oxazoline), CR'$_2$(chiral oxazoline), CH$_2$PR'$_2$, CH$_2$(o-substituted pyridine), SiR'$_3$, CR'$_2$OH or E=

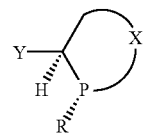

then ligands are:

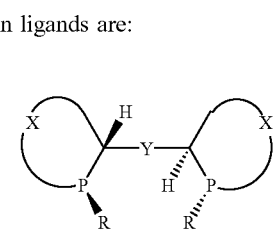

Y=(CH$_2$)$_n$, n=0, 1, 2, 3, CH$_2$NHCH$_2$, CR'$_2$, CO, SiR'$_2$, C$_5$H$_3$N, C$_6$H$_4$, alkyl substituted alkyl, divalent aryl, 2,2'divalent-1,1'biphenyl, substituted aryl, hetereoaryl, ferrocene R'=alkyl, aryl, substituted alkyl, aryl, alkylaryl, H.

In these ligands, the bridge group X for the phosphocyclic compounds are (CH2)n, n=1, 2, 3, 4, 5, 6. CH2OCH2, CH2NHCH2,, CH2CH(R')CH(R'), CH2CH(OR')CH(OR'), CH2CH(OH)CH(OH), CH2CH(OCR'2O)CH, CH2CH (OalkylO)CH, CH2CH(OCHR'O)CH, CH2NR'CH2, CH2CH2NR'CH2, CH2CH2OCH2, CH2(C6H4), CH2(Ar), CH2(hetereoaryl), CH2(alkenyl), alkyl, substituted alkyl, aryl, substituted aryl, CH2(biaryl), CH2(ferrocene). R is alkyl, aryl, substituted alkyl, substituted aryl, hetereoaryl, ferrocene. E is PR'2, PR'R'', o-substituted pyridine, oxazoline, chiral oxazoline, CH2(chiral oxazoline), CR'2(chiral oxazoline), CH2PR'2, CH2(o-substituted pyridine), SiR'3, CR'2OH.

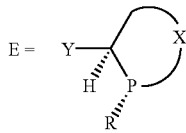

then ligands are:

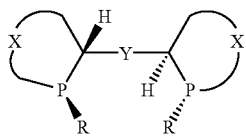

Y can be (CH2)n, n=0, 1, 2, 3, CH2NHCH2, CH2SCH2, CH2PR'CH2, CR'2, CO, SiR'2, C5H3N, C6H4, alkyl, substituted alkyl, divalent aryl, 2,2'divalent-1,1'biphenyl, substituted aryl, hetereoaryl, ferrocene. R'=alkyl, aryl, substituted alkyl, aryl, alkylaryl, H.

In a preferred embodiment, the ligand of the present invention includes compounds represented by the formulas wherein:

X can be $(CH_2)_n$ wherein n is from 1 to 6, $CH_2OCH_2$, $CH_2NHCH_2$, $CH_2CH(R')CH(R')$, $CH_2CH(OR')CH(OR')$, $CH_2NR'CH_2$, $CH_2CH(OH)CH(OH)$, $CH_2CH_2NR'CH_2$, $CH_2CH_2OCH_2$ and a group represented by the formula:

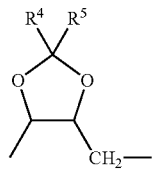

wherein each $R^4$ and $R^5$ can independently be hydrogen, alkyl, aryl, substituted alkyl and substituted aryl; and wherein:

Y can be $(CH_2)_n$ wherein n is from 0 to 3, $CH_2NHCH_2$, $CH_2SCH_2$, $CH_2PR'CH_2$, CR'2, CO, $SiR'_2$, $C_5H_3N$, $C_6H_4$, alkylene, substituted alkylene, 1,2-divalent arylene, 2,2'-divalent-1,1'-biphenyl, substituted aryl, hetereoaryl and ferrocene.

More particularly, the chiral ligand can be represented by the formula and its enantiomer:

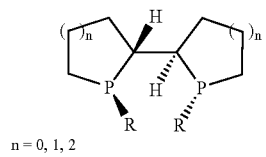

n = 0, 1, 2 wherein R can be alkyl, aryl, substituted alkyl, substituted aryl, hetereoaryl, ferrocenyl, alkoxy and aryloxy; and
wherein n is from 0 to 2;
R can be $CH_3$, Et, iPr, t-Bu, 1-adamantyl, $Et_3C$, cyclo-$C_5H_9$, cyclo-$C_6H_{11}$, phenyl, p-tolyl, 3,5-dimethylphenyl, 3,5-di-t-butyl phenyl, ortho-anisyl and naphthyl.

Examples of such ligands include a ligand represented by the formula and its enantiomer:

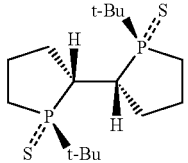

and a ligand represented by the formula and its enantiomer:

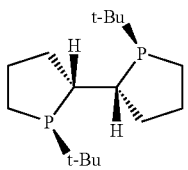

The ligands according to the present invention can be in the form of a phosphine borane, phosphine sulfide or phosphine oxide.

Selective examples of specific chiral ligands are listed below to illustrate the new P-chiral phospholanes and P-chiral phosphocyclic compounds (L1 to L35).

For each ligand, the corresponding enantiomer is also contemplated. These compounds can be prepared from corresponding phosphine-boranes, phosphine sulfides and phosphine oxides.

L1

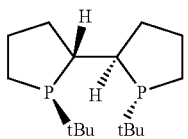

L2

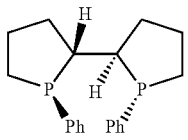

L3

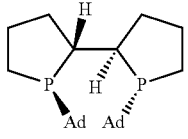

L4

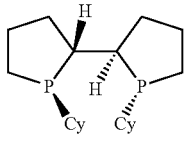

L5

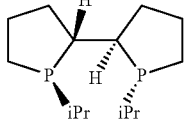

-continued
L6
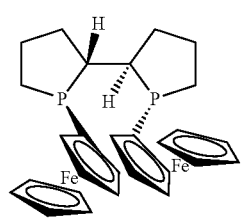
L7
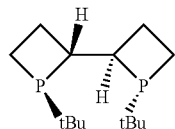
L8
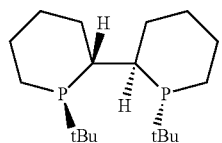
L9
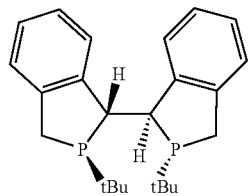
L10
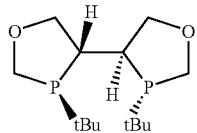
L11
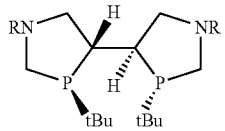
L12
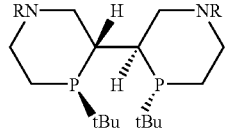
L13
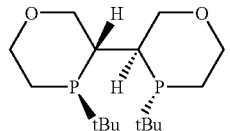
L14
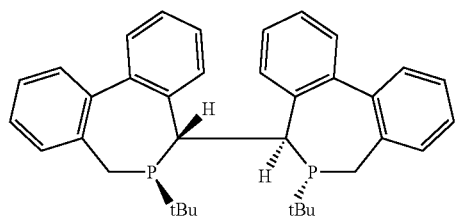
-continued
L15
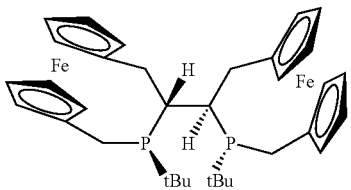
L16
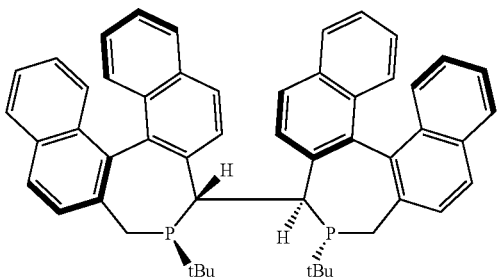
L17
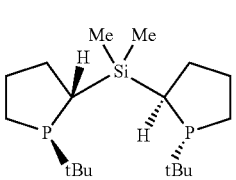
L18
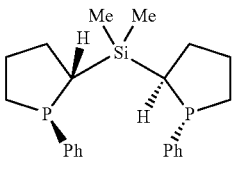
L19
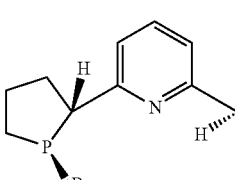
L20
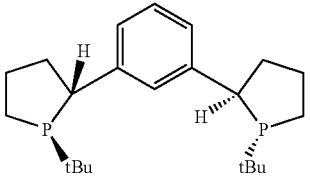
L21
L22
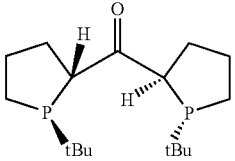

-continued
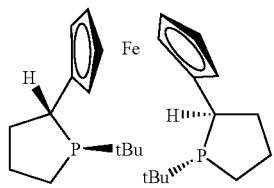
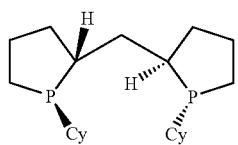
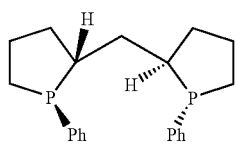
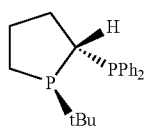
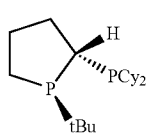
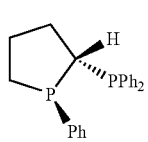
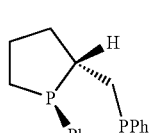
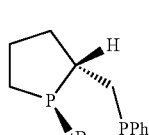
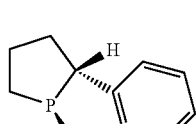
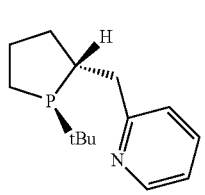
-continued
L23 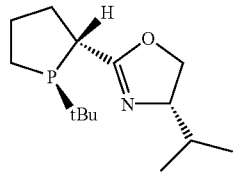
L24 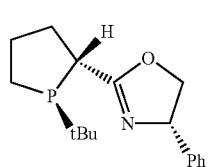
L25 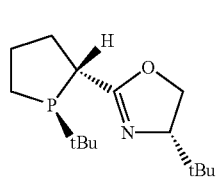
L26 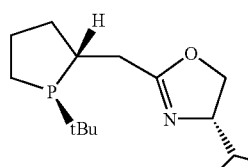
L27 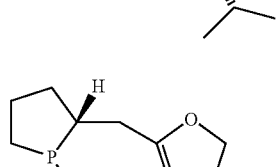
L28 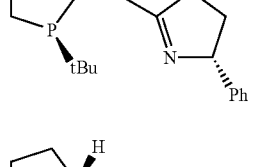
L29 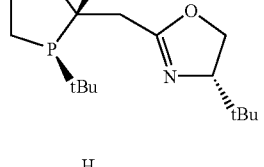
L30 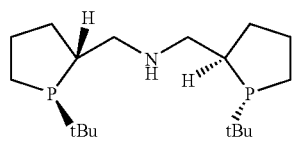
L31 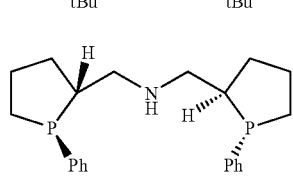
L32 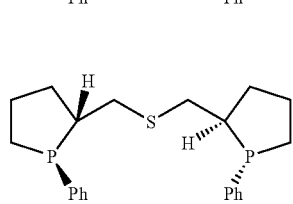
L33
L34
L35
L36
L37
L38
L39
L40
L41

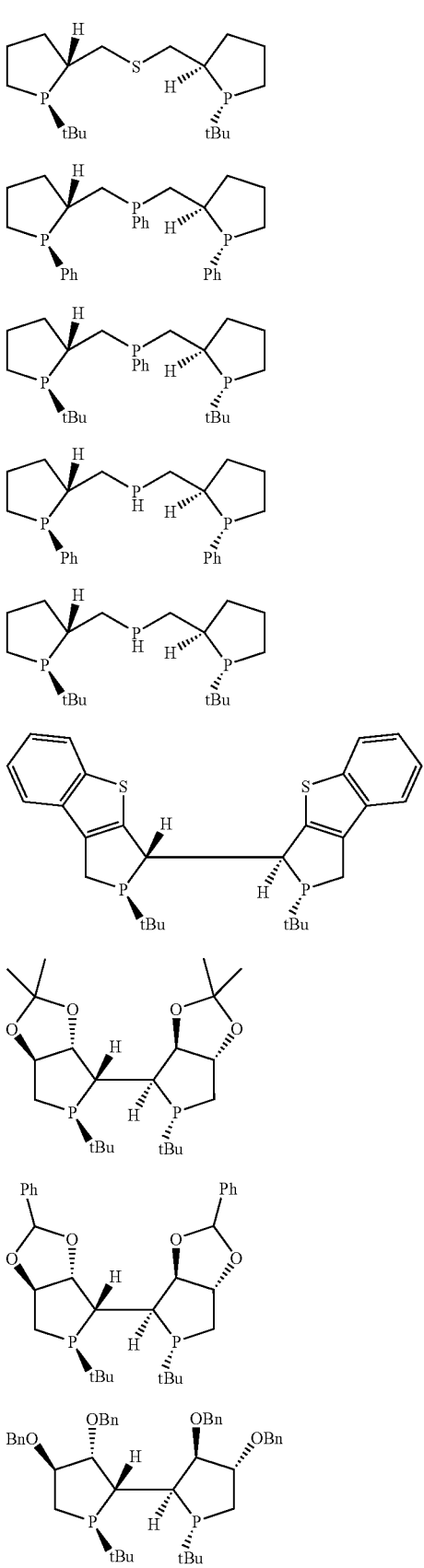

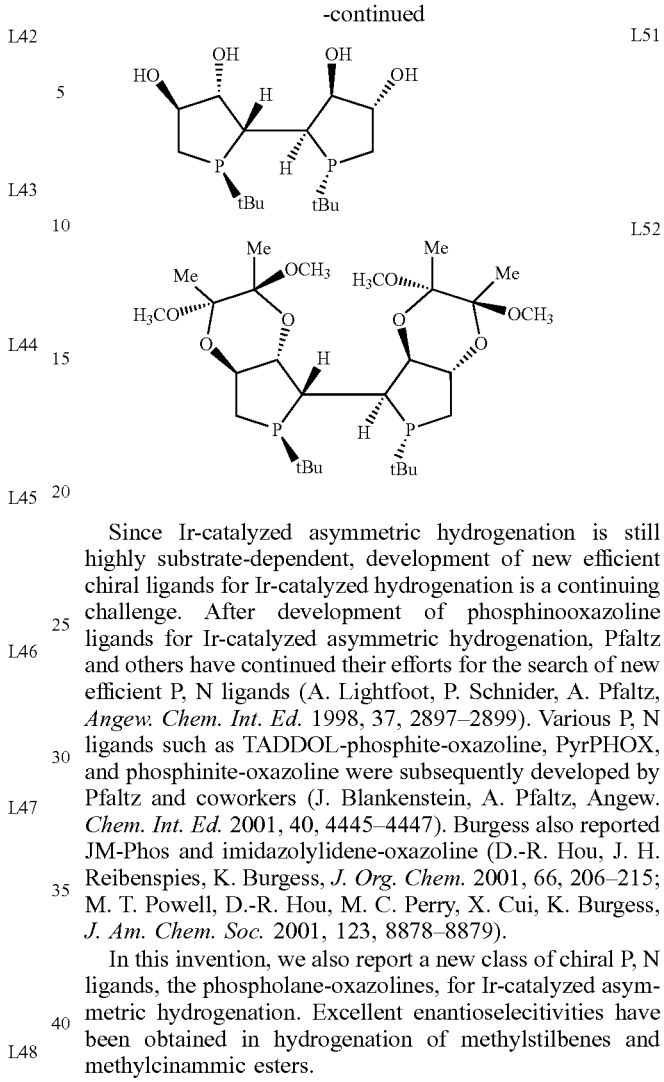

Since Ir-catalyzed asymmetric hydrogenation is still highly substrate-dependent, development of new efficient chiral ligands for Ir-catalyzed hydrogenation is a continuing challenge. After development of phosphinooxazoline ligands for Ir-catalyzed asymmetric hydrogenation, Pfaltz and others have continued their efforts for the search of new efficient P, N ligands (A. Lightfoot, P. Schnider, A. Pfaltz, Angew. Chem. Int. Ed. 1998, 37, 2897–2899). Various P, N ligands such as TADDOL-phosphite-oxazoline, PyrPHOX, and phosphinite-oxazoline were subsequently developed by Pfaltz and coworkers (J. Blankenstein, A. Pfaltz, Angew. Chem. Int. Ed. 2001, 40, 4445–4447). Burgess also reported JM-Phos and imidazolylidene-oxazoline (D.-R. Hou, J. H. Reibenspies, K. Burgess, J. Org. Chem. 2001, 66, 206–215; M. T. Powell, D.-R. Hou, M. C. Perry, X. Cui, K. Burgess, J. Am. Chem. Soc. 2001, 123, 8878–8879).

In this invention, we also report a new class of chiral P, N ligands, the phospholane-oxazolines, for Ir-catalyzed asymmetric hydrogenation. Excellent enantioselecitivities have been obtained in hydrogenation of methylstilbenes and methylcinammic esters.

The present invention further provides a catalyst prepared by a process including:

contacting a transition metal salt, or a complex thereof, and a chiral ligand according to the present invention as described herein above.

Suitable transition metals for the preparation of the catalyst include Ag, Pt, Pd, Rh, Ru, Ir, Cu, Ni, Mo, Ti, V, Re and Mn.

As mentioned above, the catalyst can be prepared by contacting a transition metal salt or its complex and a ligand according to the present invention.

Suitable transition metal salts or complexes include the following:

AgX; Ag(OTf); Ag(OTf)$_2$; AgOAc; PtCl$_2$; H$_2$PtCl$_4$; Pd$_2$(DBA)$_3$; Pd(OAc)$_2$; PdCl$_2$(RCN)$_2$; (Pd(allyl)Cl)$_2$; Pd(PR$_3$)$_4$; (Rh(NBD)$_2$)X; (Rh (NBD)Cl)$_2$; (Rh(COD)Cl)$_2$; (Rh(COD)$_2$)X; Rh(acac)(CO)$_2$; Rh(ethylene)$_2$(acac); (Rh (ethylene)$_2$Cl)$_2$; RhCl(PPh$_3$)$_3$; Rh(CO)$_2$Cl$_2$; RuHX(L)$_2$(diphosphine), RuX$_2$(L)$_2$ (diphosphine), Ru(arene)X$_2$(diphosphine), Ru(aryl group)X$_2$; Ru(RCOO)$_2$(diphosphine); Ru(methallyl)2(diphosphine); Ru(aryl group)X$_2$(PPh$_3$)$_3$; Ru(COD)(COT); Ru(COD)(COT)X; RuX$_2$(cymen); Ru(COD)$_n$; Ru(aryl group)X$_2$(diphosphine); RuCl$_2$(COD); (Ru(COD)$_2$)X; RuX$_2$(diphosphine); RuCl$_2$(=CHR)(PR'$_3$)$_2$; Ru(ArH)Cl$_2$; Ru(COD)(methallyl)$_2$; (Ir (NBD)$_2$Cl)$_2$; (Ir(NBD)$_2$)X; (Ir(COD)$_2$Cl)$_2$; (Ir(COD)$_2$)X; CuX (NCCH$_3$)$_4$; Cu(OTf); Cu(OTf)$_2$; Cu(Ar)X; CuX; Ni(acac)$_2$; NiX$_2$; (Ni(allyl)X)$_2$; Ni(COD)$_2$; MoO$_2$(acac)$_2$; Ti(O-iPr)$_4$; VO(acac)$_2$; MeReO$_3$; MnX$_2$ and Mn(acac)$_2$.

Each R and R' in these is independently selected from alkyl or aryl; Ar is an aryl group; and X is a counteranion.

In the above transition metal salts and complexes, L is a solvent and the counteranion X can be halogen, BF$_4$, B(Ar)$_4$ wherein Ar is fluorophenyl or 3,5-di-trifluoromethyl-1-phenyl, ClO$_4$, SbF$_6$, PF$_6$, CF$_3$SO$_3$, RCOO or a mixture thereof.

In another aspect, the present invention includes a process for preparation of an asymmetric compound using the catalysts described above. The process includes the step of contacting a substrate capable of forming an asymmetric product by an asymmetric reaction and a catalyst according to the present invention prepared by contacting a transition metal salt, or a complex thereof, and a ligand according to the present invention.

Suitable asymmetric reactions include asymmetric hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution and [m+n] cycloaddition wherein m=3 to 6 and n=2.

Preferably, the asymmetric reaction is hydrogenation and the substrate to be hydrogenated is an ethylenically unsaturated compound, imine, ketone, enamine, enamide, and vinyl ester.

The present invention still further includes a process for preparation of an asymmetric compound including:

contacting a substrate capable of forming an asymmetric product by an asymmetric reaction and a catalyst prepared by a process including: contacting a transition metal salt, or a complex thereof, and a chiral ligand according to the present invention as described herein above.

The present invention still further includes a process for preparing (1R, 1R', 2R, 2R')-1,1'-di-alkyl -[2,2']-diphospholanyl-1,1'-disulfide including the steps of:

asymmetrically deprotonating a 1-alkyl-phospholane-1-sulfide with n-butyllithium/(−)-sparteine in a solvent to produce an anion of the 1-alkyl-phospholane-1-sulfide; and contacting the anion of the 1-alkyl-phospholane-1-sulfide and CuCl$_2$ to oxidatively couple the anion of the 1-alkyl-phospholane-1-sulfide and produce a reaction mixture including the (1R, 1R', 2R, 2R')-1,1'-di-alkyl-[2,2']-diphospholanyl-1,1'-disulfide.

Further still, the present invention includes a process for preparing (1S, 1S', 2R, 2R')-1,1'-di-alkyl-[2,2']-diphospholanyl.

The process includes the steps of:

asymmetrically deprotonating a 1-alkyl-phospholane-1-sulfide with n-butyllithium/(−)-sparteine in a solvent to produce an anion of the 1-alkyl-phospholane-1-sulfide;

contacting the anion of the 1-alkyl-phospholane-1-sulfide and CuCl$_2$ to oxidatively couple the anion of the 1-alkyl-phospholane-1-sulfide and produce a reaction mixture comprising (1R, 1R', 2R, 2R')-1,1'-di-alkyl-[2,2']-diphospholanyl-1,1'-disulfide;

recrystallizing the (1R, 1R', 2R, 2R')-1,1'-di-alkyl-[2,2']-diphospholanyl-1,1'-disulfide from the reaction mixture; and contacting the (1R, 1R', 2R, 2R')-1,1'-di-alkyl-[2,2']-diphospholanyl-1,1'-disulfide and hexachlorodisilane in a solvent to produce (1S, 1S', 2R, 2R')-1,1'-di-alkyl-[2,2']-diphospholanyl.

Preferably, (1S, 1S', 2R, 2R')-1,1'-di-alkyl-[2,2']-diphospholanyl is (1S, 1S', 2R, 2R')-1,1'-di-tert-butyl-[2,2']-diphospholanyl, which is prepared from suitable tert-butyl group containing starting materials.

Several suitable procedures to prepare the chiral ligands according to the present invention are described herein below.

(a) Synthesis of TangPhos Using Asymmetric Deprotonation

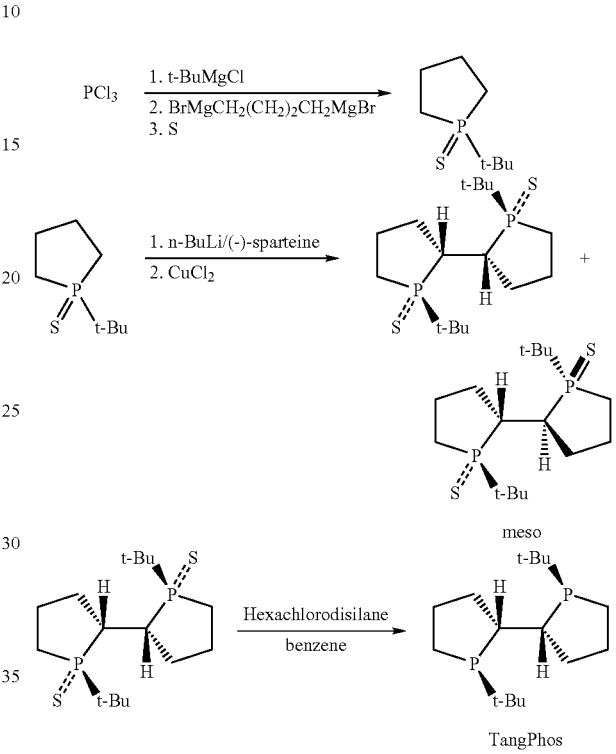

(b) Synthesis of TangPhos Through Chiral Separation

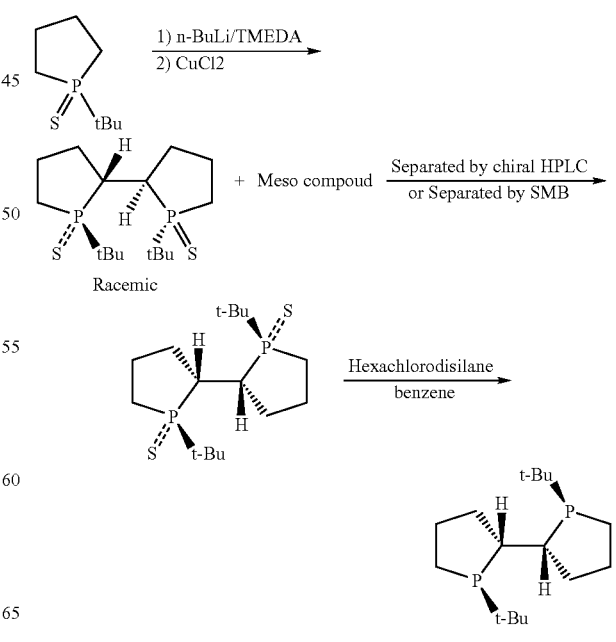

(c) Synthesis of TangPhos Ligands Through Utilization of Backbone Chirality

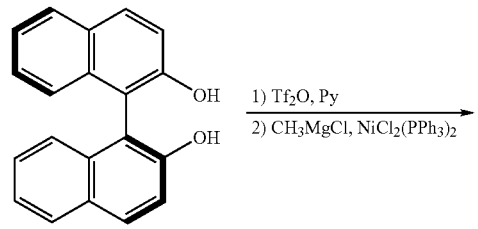

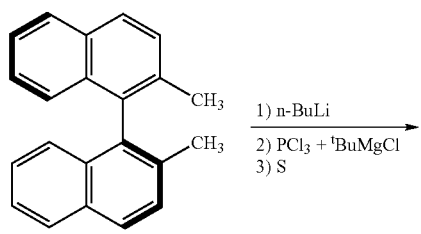

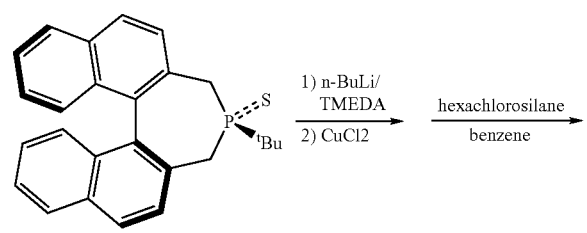

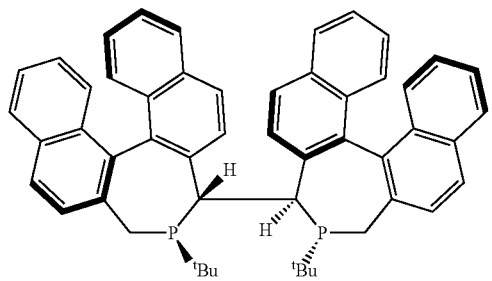

(d) Synthesis of TangPhos Ligands Through a Chiral Pool Method

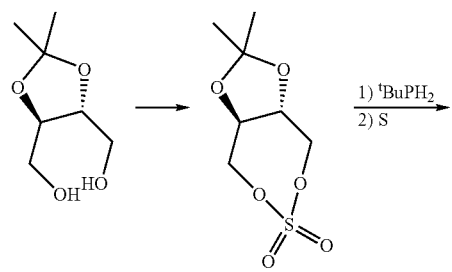

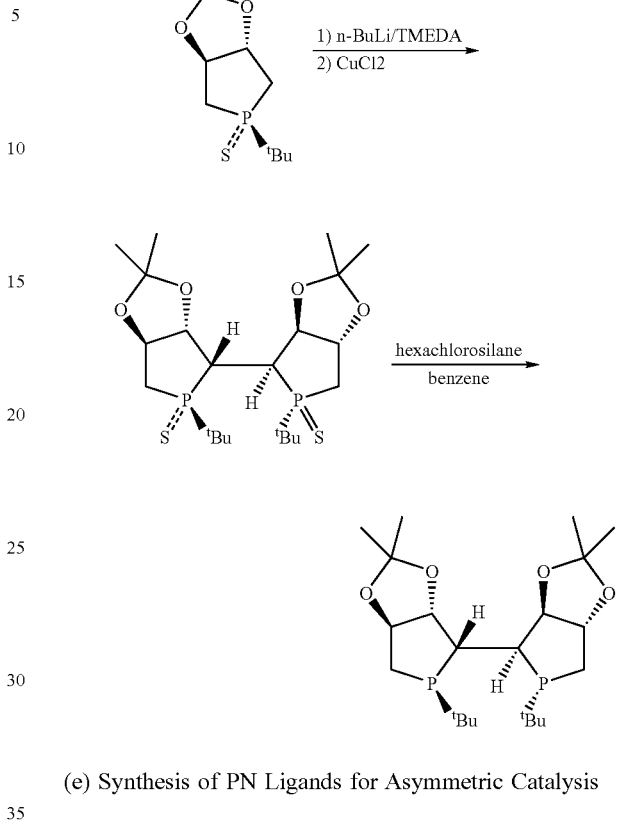

(e) Synthesis of PN Ligands for Asymmetric Catalysis

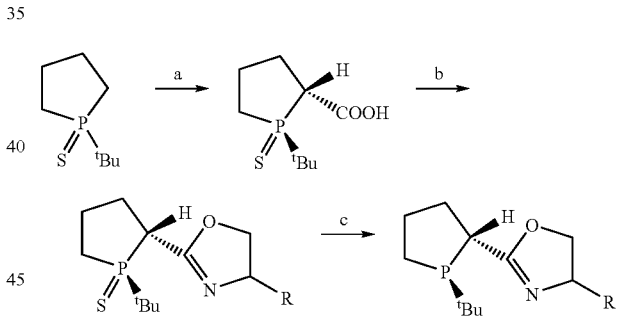

(a) nBuLi, Sparteine, $CO_2$; (b) amino alcohol, EDC, HOBT, DMF, then MsCl; (c) Raney Ni General Procedures All reactions and manipulations were performed in a nitrogen-filled glovebox or using standard Schlenk techniques. THF and toluene were dried and distilled from sodium-benzophenone ketyl under nitrogen. Methylene chloride was distilled from $CaH_2$. Methanol was distilled from Mg under nitrogen. (R, R)-BDNPB was made a solution of 10 mg/ml in toluene before use. Column chromatography was performed using EM silica gel 60 (230~400 mesh). $^1H$, $^{13}C$ and $^{31}P$ NMR were recorded on Bruker WP-200, AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Helwett-Packard 6890 gas chromatography using chiral capillary columns. HPLC analysis was carried on Waters™ 600 chromatography.

EXAMPLE 1

Synthesis of TangPhos (1)

An efficient three-step synthetic of chiral C2 symmetric P-chiral bisphospholane route has been developed.

Preparation of 1-tert-butyl-phospholane 1-sulfide

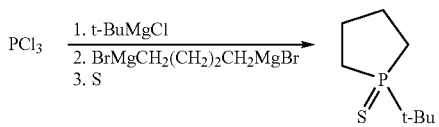

Preparation of BrMgCH$_2$(CH$_2$)$_2$CH$_2$MgBr. To a dry Schlenk flask held with magnesium turning (7.92 g, 0.33 mol) in 300 ml dry THF was added dropwise 1,4-dibromobutane (23.7 g, 0.11 mol) in 50 mL of THF at room temperature. The reaction was very exothermic during the addition. After the addition was complete (within 1 h), the resulting dark solution was kept at r.t. for 2 more hours. The whole solution was used directly for the following reaction.

To a solution of phosphorous trichloride (13.7 g, 0.10 mol) in THF (300 mL) was added dropwise a solution of t-BuMgCl in THF (100 mL, 1.0M) at −78° C. The addition was complete within 2 hrs. After the mixture was stand at −78° C. for 1 h, a solution of BrMgCH$_2$(CH)$_2$CH$_2$MgBr in THF (made above) was added dropwise. The addition was complete within 2 hrs. The mixture was then allowed to warm to r.t over 2 h and stirred overnight.

At room temperature, to the reaction mixture was added sulfur powder (4.8 g, 0.15 mol) through one portion. The resulting solution was further stirred at r.t. for 2 h. Water (300 mL) was then added. To the THF layer was added 500 mL EtOAc. The organic layer was washed with water (300 mL) followed by brine (300 mL), dried over Na$_2$SO$_4$, and concentrated. The resulting oil was passed through a silica gel column followed by recrystallization to give colorless crystalline product 1-tert-butyl-phospholane 1-sulfide 8 g (45% yield).

Synthesis of (1R, 1R', 2R, 2R')-1,1'-di-tert-butyl-[2, 2']-diphospholanyl 1,1'-disulfide

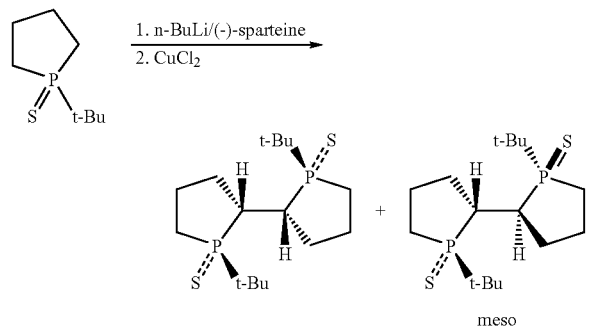

At −78° C., to a solution of (−)-sparteine (7.83 mL, 34 mmol) in ether (200 mL) was added n-butyllithium (21.3 mL, 34 mmol, 1.6M in hexane) dropwise. The resulting solution was kept at −78° C. for 30 min. Then at this temperature, to the solution was added dropwise a solution of 1-tert-butyl-phospholane 1-sulfide (5.0 g, 28.4 mmol in ether (100 mL). The addition was complete within 1 hr. The resulting mixture was kept at −78° C. and stirred for 8 more hrs. Then dry CuCl$_2$ (5.73 g, 42.6 mmol) was added into the solution through one portion. The resulting suspension was vigorously stirred and allowed to warm to r.t. over 4 hrs. 150 ml of concentrated ammonia was added. The water layer was washed twice with EtOAc (2×100 mL). The combined organic phase was further washed in a sequence with 5% ammonia (100 mL), 1 N HCl (100 mL), water (100 mL), and brine (100 mL). After dried over Na$_2$SO$_4$, the solution was concentrated under reduced pressure to give an oily solid, which was subsequently purified by passing a silica gel column to give a solid mixture (4 g) of (1R, 1R', 2R, 2R')-1,1'-di-tert-butyl-[2,2']-diphospholanyl 1,1'-disulfide (72% ee, 83%) and meso compound (1R, 1R', 2S, 2S')-1, 1'-di-tert-butyl-[2,2']-diphospholanyl 1,1'-disulfide (17%).

The mixture was recrystallized from ethyl acetate and ethanol to give 700 mg of pure product (1R, 1R', 2R, 2R')-1,1'-di-tert-butyl-[2,2']-diphospholanyl 1,1'-disulfide (ee: >99% according to HPLC, total yield: 14%).

Synthesis of (1S, 1S', 2R, 2R')-1, 1'-di-tert-butyl-[2, 2']-diphospholanyl TangPhos (1)

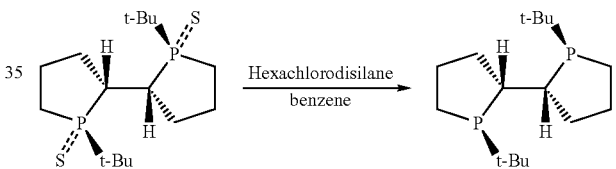

To a solution of (1R, 1R', 2R, 2R')-1,1'-di-tert-butyl-[2, 2']-diphospholanyl 1,1'-disulfide (440 mg, 1.26 mmol) in 25 ml benzene was added hexachlorodisilane (3.25 mL, 5.08 g, 18.9 mmol). The mixture was stirred at reflux for 4 h. After the solution was cooled to r.t., 50 mL of degassed 30% (w/w) NaOH solution was carefully added to the reaction mixture with an ice-water bath. The resulting mixture was then stirred at 60° C. until the aqueous layer became clear. The two phases were separated. The water phase was washed twice with degassed benzene (2×30 mL). The combined benzene was dried over Na$_2$SO$_4$ and concentrated.

The solid residue was re-dissolved in a minimum amount of degassed dichloromethane, which was subsequently passed through a basic Al$_2$O$_3$ plug (eluent: Et$_2$O:hexane=1:10) to give pure white product (1) 320 mg (88% yield).

EXAMPLE 2

Asymmetric Hydrogenation of Dehydroamino Acids General Procedure for Asymmetric Hydrogenation To a solution of [Rh(COD)$_2$]BF$_4$ (5.0 mg, 0.012 mmol) in THF (10 mL) in a glovebox was added a chiral phosphine ligand (TangPhos 0.15 mL of 0.1 M solution in toluene, 0.015 mmol). After stirring the mixture for 30 min, the dehydroamino acid (1.2 mmol) was added. The hydrogenation was performed at rt under 20 psi of hydrogen for 24 h. The reaction mixture was treated with $CH_2N_2$, then concentrated in Vacuo. The residue was passed through a short silica gel column to remove the catalyst. The enantiomeric excesses were measured by GC using a Chirasil-VAL III FSOT column.

The absolute configuration of products was determined by comparing the observed rotation with the reported value. All reactions went in quantitative yield with no by-products found by GC.

Asymmetric hydrogenation for making alpha amino acid derivatives using TangPhos (1) as the ligand is shown in the Table below:

Asymmetric Hydrogenation of Dehydroamino Acid Derivatives[a]

Ar—C(COOR)=CH—NHAc + $H_2$ → [Rh(NBD)$_2$]SbF$_6$ (1 mol %) + TangPhos (1.1 mol %) / $CH_3OH$, 12 h, rt → Ar—CH$_2$—CH(COOR)(NHAc) (R)[b,c]

| Entry | Substrate | ee[c] (%) |
|---|---|---|
| 1 | Ar = Ph, R = H | >99[d] |
| 2 | Ar = Ph, R = CH3 | >99 |
| 3 | Ar = p-F—Ph, R = H | 99[d] |
| 4 | Ar = p-F—Ph, R = CH3 | >99 |
| 5 | Ar = p-MeO—Ph, R = H | >99[d,e] |
| 6 | Ar = p-MeO—Ph, R = CH3 | >99 |
| 7 | Ar = m-Br—Ph, R = H | >99[d] |
| 8 | Ar = m-Br—Ph, R = CH3 | >99 |
| 9 | Ar = o-Cl—Ph, R = H | >99[d] |
| 10 | Ar = o-Cl—Ph, R = CH3 | >99 |
| 11 | Ar = 2-thienyl, R = H | >99[d] |
| 12 | Ar = 2-thienyl, R = CH3 | >99 |
| 13 | Ar = 2-naphthyl, R = H | >99[d] |
| 14 | Ar = 2-naphthyl, R = CH3 | >99 |
| 15 | Ar = Ph, R = H, N-benzoyl | >99[d] |
| 16 | Ar = Ph, R = CH3, N-benzoyl | >99 |

[a]The reaction eas carried out at rt under 20 psi of $H_2$ for 24 h. The catalyst was made in situ by stirring a solution of [Rh(NBD)$_2$]SbF$_6$ and TangPhos in methanol (2 mL) [substrate:[Rh]:TangPhos = 1:0.01:0.011]. The reaction went with 100% conversion.
[b]The R absolute configuration was assigned by comparison of optical rotation with reported data.
[c]Enantiomeric excesses were determined by chiral GC using a Chrialsil-VAL III FSOT column.
[d]Determined on corresponding methyl ester.
[e]The % ee was determined by HPLC using a Daicel Chiralcel OJ column.

EXAMPLE 3

Asymmetric Synthesis of Beta-Amino Acid Derivatives Synthesis of Starting Material 3-Acetamido-3-Aryl-2-Propenoates and 3-Acetamido-3-hetero-Aryl-2-Propenoates Typical procedure: The starting material methyl 3-acetamido-3-phenyl-2-propenoate can be conveniently synthesized from cheap acetophenone in three steps according to known literature procedure in good yields. The literatures are Zhu, G.; Zhen, Z.; Zhang, X. *J. Org. Chem.* 1999, 64, 6907–6910; Krapcho, A. P.; Diamanti, *J. Org. Synth.* 1973, 5, 198–201. $^1$H-NMR (CDCl$_3$, 360 MHz) δ (Z isomer) 2.17 (s, 3H), 3.77 (s, 3H), 5.29 (s, 1H), 7.37–7.45 (m, 5H); (E isomer) 2.38 (s, 3H), 3.77 (s, 3H), 6.65 (s, 1H), 7.37–7.45 (m, 5H).

Hydrogenation for Making Beta Amino Acid Derivatives with the Rh-TangPhos (1) System R$_1$—C(=CH—COOR$_2$)—NHAc → [Rh(TangPhos)nbd]SbF6 / rt, H2 (20 psi), 24 h, THF → R$_1$—CH(NHAc)—CH$_2$—COOR$_2$

| entry[a] | R$_1$ | R$_2$ | geo m.[c] | ee[b] (%) | config. |
|---|---|---|---|---|---|
| 1 | Me | Et | E | 99.5 | R |
| 2 | Me | Et | Z | 97.3 | R |
| 3 | Me | i-Pr | E | 99.3 | R |
| 4 | Et | Me | E | 99.6 | R |
| 5 | n-Pr | Et | E | 99.6 | R |
| 6 | i-Bu | Me | E | 98.5 | R |
| 7 | Ph | Me | E/Z | 93.8 | S |
| 8 | p-F—Ph | Me | E/Z | 95.0 | S |
| 9 | p-Cl—Ph | Me | E/Z | 92.3 | S |
| 10 | p-Br—Ph | Me | E/Z | 95.1 | S |
| 11 | p-Me—Ph | Me | E/Z | 94.0 | S |
| 12 | p-MeO—Ph | Me | E/Z | 98.5[d] | S |
| 13 | p-BnO—Ph | Me | E/Z | 98.5 | S |
| 14 | o-Me—Ph | Me | E/Z | 74.3 | S |
| 15 | o-MeO—Ph | Me | E/Z | 83.1 | S |

[a]The reactions were carried out under 20 psi of $H_2$ in THF at rt for 24 h. Substrate/[Rh(TangPhos)nbd]SbF$_6$ = 200:1. The absolute configurations were determined by comparing the optical rotations with reported values.
[b]The ee (%) values were determined by chiral GC using a Chiralselect 1000 column.
[c]For the E/Z ratios of E/Z mixtures.
[d]The ee was determined by chiral HPLC using (s, s)-whelk-01 column For general synthetic procedures of β-aryl β-acetamidoacrylate esters, see Zhou, Y.-G.; Tang, W.; Wang, W.-B.; Li, W.; Zhang, X. *J. Am. Chem. Soc.* 2002, 124, 4952–4953. For general synthetic procedure of β-alkyl β-acetamidoacrylate esters, see Zhu, G.; Chen, Z.; Zhang, X. *J. Org. Chem.* 1999, 64, 6907–6910. For analytical data of known substrates and products, please also refer to the two aforementioned papers.

Methyl 3-Acetamido-3-(4-benzyloxyphenyl)-2-propenoate

Z/E=9:1; $^1$H NMR (360 MHz, CDCl$_3$) δ (Z isomer) 2.06 (s, 3H), 3.65 (s, 3H), 4.98 (s, 2H), 5.18 (s, 1H), 6.86 (d, J=6.8 Hz, 2H), 7.28 (m, 7H), 10.46 (s, 1H); (E isomer) 2.27 (s, 3H), 3.65 (s, 3H), 4.98 (s, 2H), 6.44 (s, 1H), 6.86 (d, J=6.8 Hz, 2H), 7.28 (m, 7H).

General Procedure for Asymmetric Hydrogenation of β-alkyl or β-aryl β-acetamidoacrylic esters To a solution of P-acetamidoacrylic ester (0.5 mmol) in 4 mL of degassed THF Rh[(TangPhos)nbd]SbF$_6$ (2.5 μmol) was added in a glovebox filled with nitrogen. The whole solution was transferred into an autoclave.

The autoclave was then purged three times with hydrogen and filled with hydrogen with 20 psi pressure. The resulting reactor was stirred at room temperature for 24 hr. After release of the hydrogen, the autoclave was opened and the reaction mixture was evaporated.

The residue was passed through a short silica gel plug to give hydrogenation product β-amino acid derivatives. A small amount of sample was subjected to chiral GC or HPLC analysis.

Methyl 3-acetamido-3-(4-benzyloxyphenyl)-propanoate 98.5% ee, $[\alpha]^{25}{}_D$=−79.5°; $^1$H NMR (300 MHz, CDCl$_3$) δ 2.00 (s, 3H), 2.83 (dd, J=15.7, 6.2 Hz, 1H), 2.93 (dd, J=15.6, 6.0 Hz, 1H), 3.63 (s, 3H), 5.05 (s, 2H), 5.40 (m, 1H), 6.93 (d, 1H), 6.94 (dd, J=6.7, 2.0 Hz, 2H), 7.23 (dd, J=6.8, 1.8 Hz, 2H), 6.72 (m, 5H); $^{13}$C NMR (75 MHz, CDCl$_3$) δ 23.8, 40.2, 49.5, 52.2, 115.4, 127.9, 128.0, 128.4, 129.0, 133.3, 137.3, 158.6, 169.7, 172.1; MS (ESI) m/z 328 (M$^+$+1); HRMS calculated for C$_{19}$H$_{22}$NO$_4$ 3281549, found 328.1553. Chiral HPLC conditions ((s, s)-whelk-01): solvent hexane:isopropanol(1:1); flow rate 1 mL/min; retention time 8.2 min (R), 13.1 min (S).

EXAMPLE 4

Asymmetric Hydrogenation of Enamides

Table. Rh-Catalyzed Asymmetric Hydrogenation of α-Arylenamides Using TangPhos (1)

| Entry | Substrate Ar | R | ee [%][b] |
|---|---|---|---|
| 1 | Ph | H | >99 |
| 2 | m-Me—Ph | H | >99 |
| 3 | p-CF$_3$—Ph | H | >99 |
| 4 | p-Cy—Ph | H | >99 |
| 5 | p-Ph—Ph | H | 99 |
| 6 | 2-naphthyl | H | >99 |
| 7 | Ph | CH$_3$ | 98 |
| 8 | p-CF$_3$—Ph | CH$_3$ | 98 |
| 9 | p-MeO—Ph | CH$_3$ | 98 |
| 10 | 2-naphthyl | CH$_3$ | 99 |
| 11 | Ph | CH(CH$_3$)$_2$ | 98 |
| 12 | Ph | CH$_2$Ph | 99 |
| 13 | | | 97 |

[a]Conditions: see Experimental Section for details. Enamides were prepared according to the literature method.
[b]The R absolute configuration was assigned by comparison of optical rotation with reported data. ee's were determined by chiral GC using Supelco Chiral Select 1000 column or by chiral HPLC with a (R, R)-Poly Whelk-01 column.

EXAMPLE 5

High Turnovers for Asymmetric Hydrogenation of Enamides Using Rh(TangPhos 1) Catalyst Asymmetric hydrogenation with [Rh(NBD)TangPhos (1)]$^+$SbF$_6{}^-$ as the catalyst:

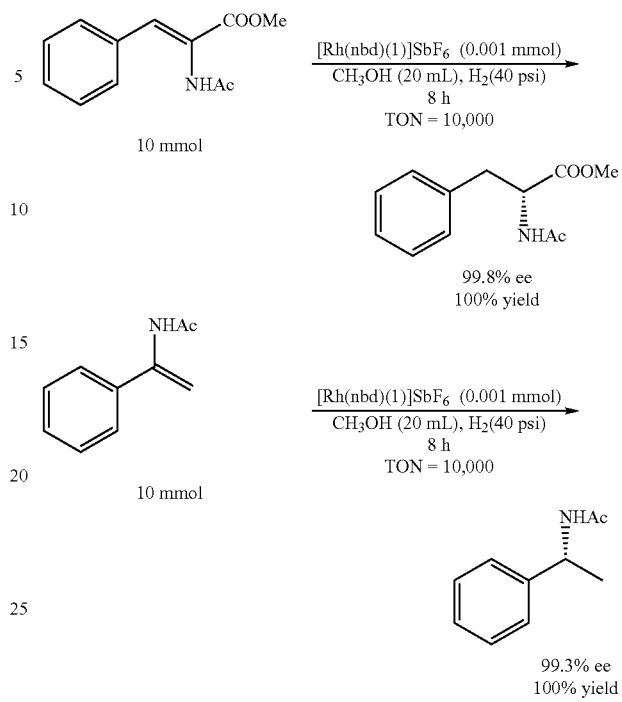

Procedure for Hydrogenation of α-dehydro Amino Acid

To a solution of methyl α-(acetylamino)-2-phenylacrylate (2.19 g, 10 mmol) in 20 mL of degassed methanol in glovebox was added [Rh(nbd)(1)]SbF$_6$(1 ml of 0.001M solution in methanol, 0.001 mmol). The hydrogenation was performed at room temperature under 40 psi of H$_2$ for 8 h. After carefully releasing the hydrogen, the reaction mixture was passed through a short silica gel column to remove the catalyst. The enantiomeric excesses of (R)-methyl 2-acetylamino-3-phenylpropionate were measured by chiral GC directly. (Conversion: 100%, ee: 99.8%, TON: 10,000)

EXAMPLE 6

Asymmetric Hydrogenation of Itaconic Acid Derivatives with Rh(TangPhos (1) Catalyst

| entry | R$_1$ | R$_2$[b] | ee (%)[c] |
|---|---|---|---|
| 1 | H | H | 99 |
| 2 | CH$_3$ | CH(CH$_3$)$_2$ | 96 |
| 3 | CH$_3$ | Ph | 93 |
| 4 | CH$_3$ | p-MeO—Ph | 97 |
| 5 | CH$_3$ | p-Me—Ph | 97 |
| 6 | CH$_3$ | p-Cl—Ph | >99 |
| 7 | CH$_3$ | m-Cl—Ph | 99 |
| 8 | CH$_3$ | 1-naphthyl | 99 |
| 9 | CH$_3$ | 2-naphthyl | 99 |

-continued

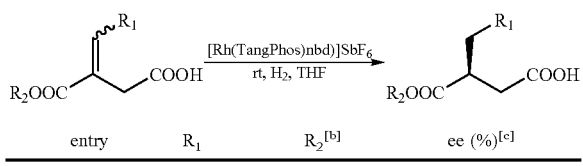

| entry | $R_1$ | $R_2$[b] | ee (%)[c] |
|---|---|---|---|

[a]Conditions: catalyst precursor = [Rh(TangPhos)(nbd)]SbF$_6$ (1 mol %), room temperature, 20 psi H$_2$, THF. The absolute configuration of product was determined by comparison with reported data.
[b]Most substrates (except entry 1) employed as crude E/Z mixtures ranging from 2/1 to >10/1.
[c]Determined on chiral GC or HPLC column after conversion of the hydrogenation product into dimethyl ester.

EXAMPLE 7

Asymmetric Hydrogenation of Arylenol Acetates with the [Rh(TangPhos (1)]Catalyst

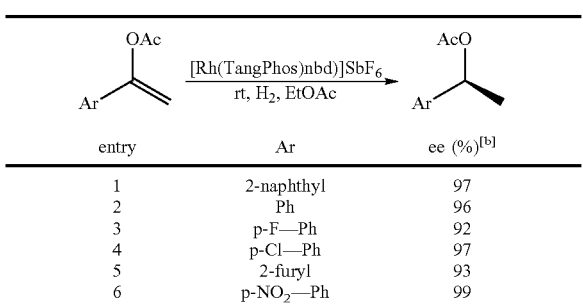

| entry | Ar | ee (%)[b] |
|---|---|---|
| 1 | 2-naphthyl | 97 |
| 2 | Ph | 96 |
| 3 | p-F—Ph | 92 |
| 4 | p-Cl—Ph | 97 |
| 5 | 2-furyl | 93 |
| 6 | p-NO$_2$—Ph | 99 |

[a]Conditions: catalyst precursor = [Rh(TangPhos)(nbd)]SbF$_6$ (1 mol %), room temperature, 20 psi H$_2$, EtOAc. The absolute configuration of product was determined by comparison with reported data.
[b]Determined on a chiral GC column (chiral select 1000).

EXAMPLE 8

Synthesis of Chiral PN Ligands for Asymmetric Catalysis

Since Ir-catalyzed asymmetric hydrogenation is still highly substrate-dependent, development of new efficient chiral ligands for Ir-catalyzed hydrogenation is a continuing challenge. A new class of chiral P, N ligands, the phospholane-oxazolines have been developed as follows:

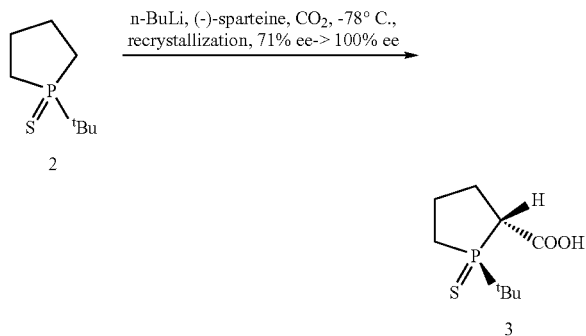

At −78° C., to a solution of (−)-sparteine (14.4 mL, 62.5 mmol) in ether (100 mL) was added dropwise n-BuLi (1.6M in hexane, 39 mL, 62.5 mmol). The mixture was stirred at −78° C. for 30 min. A solution of 2 (10 g, 56.8 mmol) in ether (150 mL) was added dropwise. The addition was complete in 1 h. The resulting reaction mixture was allowed to warm to rt and stirred overnight. The mixture was re-cooled to −78° C. Through the suspension was bubbled CO$_2$ for 2 h. Then it was quenched with the addition of 1N HCl (200 mL) followed by EtOAc (200 mL). The organic layer was washed sequentially with 1N HCl (200 mL), H$_2$O (200 mL), and brine (100 mL). The solution was dried over Na$_2$SO$_4$ and evaporated. The residue was treated with 2 N NaOH solution (300 mL). The resulting clear solution was neutralized by the addition of 2 N HCl. The precipitate was collected through vacuum filtration to give the product (8.0 g, 72% ee, 64% yield). The ee was determined by converting the product into its corresponding methyl ester by treatment with TMSCHN$_2$ in THF/CH$_3$OH solution (HPLC conditions for the methyl ester: Chiralpak AD column; hex:ipr=95:5; 8.8 min, 11.3 min.) A sample of product (7.5 g) was recrystallized twice from ethanol to give 4.5 g of enantiomerically pure product 3 (>99.9% ee, 40% total yield).

3: $[\alpha]_D^{20}$=16.9°(c=0.9, CHCl$_3$); $^1$H NMR (360 MHz, CDCl$_3$) δ 1.35 (d, $^3J_{HP}$=17.0 Hz, 9H), 1.71 (m, 1H), 2.18 (m, 3H), 2.47 (m, 2H), 3.34 (m, 1H); $^{13}$C NMR (90 MHz, CD$_3$OD) δ 25.4 (d, $^2J_{CP}$=1.7 Hz), 26.0 (d, $^2J_{CP}$=2.2 Hz), 31.3 (d, $^2J_{CP}$=7.3 Hz), 32.8 (d, $J_{CP}$=48.8 Hz), 36.1 (d, $J_{CP}$=44.1 Hz), 46.4 (d, $J_{CP}$=36.0), 172.9; $^{31}$P NMR (145 MHz, CD$_3$OD) δ 89.3 (s); APCI MS 121 (M$^+$+H); HRMS calculated for C$_9$H$_{18}$PSO$_2$ 221.0765, found 221.0762.

The methyl ester of 3: $[\alpha]_D^{20}$=42.6° (C=1, CHCl$_3$); $^1$H NMR (360 MHz, CDCl$_3$) δ 1.21 (d, $^3J_{HP}$=16.8 Hz, 9H), 1.69 (m, 1H), 1.92 (m, 2H), 2.30 (m, 3H), 3.23 (m, 1H), 3.66 (s, 3H); $^{13}$C NMR (90 MHz, CDCl$_3$) δ 25.2 (d, 2.7 Hz), 25.4 (d, $^2J_{CP}$=1.8 Hz), 29.9 (d, $^2J_{CP}$=7.4 Hz), 31.7 (d, $J_{CP}$=47.9 Hz), 35.3 (d, $J_{CP}$=43.5 Hz), 45.4 (d, $J_{CP}$=35.5 Hz), 52.7, 170.0; $^{31}$P NMR (145 MHz, CDCl$_3$) δ 87.8; APCI MS 235 (M$^+$+H); HRMS calculated for C$_{10}$H$_{20}$PSO$_2$ 235.0922 found 235.0909.

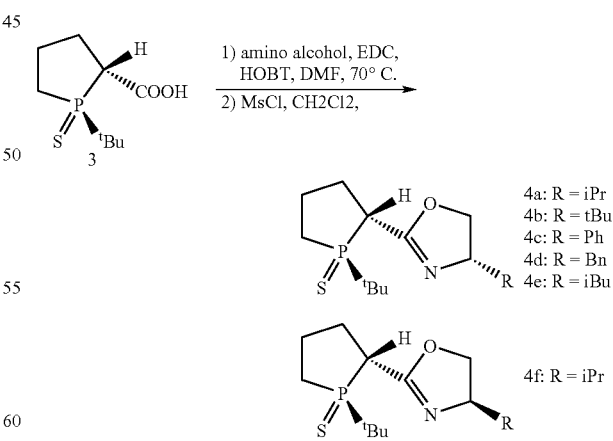

A mixture of 3 (2.27 mmol), EDC.HCl (1.3 g, 6.82 mmol), HOBT.H$_2$O (0.52 g, 3.41 mmol), chiral amino alcohol (3.41 mmol), triethylamine (1.9 mL, 13.6 mmol) in 10 mL of DMF was stirred at 70° C. overnight. To the cooled mixture was added 30 mL of 2 N HCl solution. The resulting mixture was then extracted with ethyl acetate. The organic layer was washed with water and brine, dried over Na$_2$SO$_4$. After removal of the solvent, the residue was purified by column chromatography to give condensation product in 70–80% yield.

To a mixture of condensation product (1.67 mmol), diisopropylethylamine (1.98 mL, 6.68 mmol) and triethylamine (1.38 mL, 16.7 mmol) in 10 mL of CH$_2$Cl$_2$ was added 258 µL (3.34 mmol) of methanesulfonylchloride at 0° C. After addition, the resulting mixture was allowed to warm to room temperature and stirred overnight. The solvent was removed. The residue was redissolved in ethyl acetate, washed with water and brine, and dried over Na$_2$SO$_4$. After removal of solvent, the crude product was purified by column chromatography to give pure 4a–f in 70–80% yield.

4a: $[\alpha]^{20}_D$=−75.1° (c=0.9, CHCl$_3$), $^1$H NMR (360 MHz, CDCl$_3$) δ 0.81 (d, 6.8 Hz, 3H), 0.89 (d, 6.8 Hz, 3H), 1.24 (d, $^3J_{HP}$=16.5 Hz, 9H), 1.58 (m, 1H), 1.71 (m, 1H), 1.90 (m, 1H), 2.11 (m, 2H), 2.37 (m, 2H), 3.19 (m, 1H), 3.86 (m, 1H), 3.94 (t, 7.9 Hz, 1H), 4.21 (t, 8.1 Hz, 1H); $^{13}$C NMR (90 MHz, CDCl$_3$) δ 18.7, 19.4, 25.4 (m), 30.6 (d, $^2J_{CP}$=7.9 Hz), 31.8 (d, J$_{CP}$=47.5 Hz), 32.0, 33.1, 35.2 (d, J$_{CP}$=43.4 Hz), 38.8 (d, J$_{CP}$=39.5 Hz), 70.6, 72.4, 163.9; $^{31}$P NMR (145 MHz, CDCl$_3$) δ 88.0; APCI MS 288 (M$^+$+H); HRMS calculated for C$_{14}$H$_{27}$NOPS 288.1551 found 288.1549.

4b: $[\alpha]^{20}_D$=−75.9° (c=0.9, CHCl$_3$), $^1$H NMR (360 MHz, CDCl$_3$) δ 0.83 (s, 9H), 1.25 (d, $^3J_{HP}$=16.4 Hz, 9H), 1.56 (m, 1H), 1.87 (m, 1H), 2.14 (m, 2H), 2.38 (m, 2H), 3.21 (m, 1H), 3.83 (m, 1H), 4.01 (t, 8.4 Hz, 1H), 4.16 (t, 8.5 Hz, 1H); $^{13}$C NMR (90 MHz, CDCl$_3$) δ 25.6 (d, $^2J_{CP}$=1.6 Hz), 26.5, 30.6 (d, $^2J^{CP}$=7.9 Hz), 31.9 (d, J$_{CP}$=47.2 Hz), 32.0, 33.8, 35.3 (d, J$_{CP}$=43.6 Hz), 38.9 (d, J$_{CP}$=40.0 Hz), 69.1, 75.9, 163.9; $^{31}$P NMR (145 MHz, CDCl$_3$) δ 87.3; ESI MS 302 (M$^+$+H); HRMS calculated for C$_{15}$H$_{29}$NOPS 302.1707 found 302.1716.

4c: $[\alpha]^{20}_D$=−98.9°(c=1, CHCl$_3$), $^1$H NMR (360 MHz, CDCl$_3$) δ 1.24 (d, $^3J_{HP}$=16.6 Hz, 9H), 1.58 (m, 1H), 1.91 (m, 1H), 2.16 (m, 2H), 2.39 (m, 2H), 3.28 (m, 2H), 3.19 (t, 8.3 Hz, 1H), 4.58 (t, 8.3 Hz, 1H), 5.14 (m, 1H), 7.19 (m, 5H); $^{13}$C NMR (90 MHz, CDCl$_3$) δ 25.0 (d, $^2J_{CP}$=1.1 Hz), 30.2 (d, $^2J_{CP}$=7.7 Hz), 31.3 (d, J$_{CP}$=47.3 Hz), 31.5, 34.8 (d, J$_{CP}$=43.4 Hz), 38.6 (d, J$_{CP}$=39.2 Hz), 69.6, 74.9, 127.3 (m), 142.3, 165.2 (d, $^2J_{CP}$=4.6 Hz); $^{31}$P NMR (145 MHz, CDCl$_3$) δ 88.8; APCI MS 322 (M$^+$+H); HRMS calculated for C$_{17}$H$_{25}$NOPS 322.1395 found 322.1409.

4d: $[\alpha]^{20}_D$=−54.2°(c=1, CHCl$_3$), $^1$H NMR (360 MHz, CDCl$_3$) δ 1.17 (d, $^3J_{HP}$=16.5 Hz, 9H), 1.52 (m, 1H), 1.84 (m, 1H), 2.07 (m, 2H), 2.32 (m, 2H), 2.58 (dd, 8.2 Hz, 13.6 Hz, 1H), 2.98 (dd, 5.5 Hz, 13.6 Hz,1H), 3.06 (dd, 9.6 Hz, 17.3 Hz, 1H), 3.88 (t, 7.3 Hz, 1H), 4.09 (t, 8.5 Hz), 4.3 (m, 1H), 7.13 (m, 5H); $^{13}$C NMR (90 MHz, CDCl$_3$) δ24.4, 24.6 (d, $^2J_{CP}$=1.2 Hz), 29.8 (d, $^2J_{CP}$=8.0 Hz), 30.9 (d, J$_{CP}$=47.4 Hz), 34.3 (d, J$_{CP}$=43.6 Hz), 37.8 (d, J$_{CP}$=39.1 Hz), 41.5, 66.8, 71.3, 125.8, 127.9, 128.8 (m), 163.7 (d, $^2J_{CP}$=4.7 Hz); $^{31}$P NMR (145 MHz, CDCl$_3$) δ88.5; APCI MS 336 (M$^+$+H); HRMS calculated for C$_{18}$H$_{27}$NOPS 336.1551 found 336.1542.

4e: $[\alpha]^{20}_D$=−83.9°(c=1, CHCl$_3$), $^1$H NMR (360 MHz, CDCl$_3$) δ 0.67 (t, 6.4 Hz, 6H), 1.04 (d, $^3J_{HP}$=16.4 Hz, 9H), 1.43 (m, 3H), 1.67 (m, 1H), 1.94 (m, 2H), 2.19 (m, 2H), 3.00 (m, 1H), 3.60 (t, 7.4 Hz, 1H), 3.91 (m, 1H), 4.08 (m, 8.5 Hz, 1H); $^{13}$C NMR (90 MHz, CDCl$_3$) δ22.3, 22.5, 24.4, 24.6, 24.9, 29.8 (d, $^2J_{CP}$=7.9 Hz), 30.9 (d, J$_{CP}$=47.4 Hz), 31.4 Hz, 34.3 (d, J$_{CP}$=43.4 Hz), 37.9 (d, J$_{CP}$=39.4 Hz), 45.3, 64.1, 72.6, 162.9 (d, $^2J_{CP}$=4.6 Hz); $^{31}$P NMR (145 MHz, CDCl$_3$) δ 88.0; ESI MS 302 (M$^+$+H); HRMS calculated for C$_{15}$H$_{28}$NOPS 302.1708 found 302.1715.

4f: $[\alpha]^{20}_D$=+28.6°(c=0.9, CHCl$_3$), $^1$H NMR (360 MHz, CDCl$_3$) δ 0.82 (d, 6.7 Hz, 3H), 0.94 (d, 6.7 Hz, 3H), 0.95 (d, J$_{HP}$=16.4 Hz, 9H), 1.58 (m, 1H), 1.75 (m, 1H), 1.89 (m, 1H), 2.13 (m, 2H), 2.39 (m, 2H), 3.11 (m, 1H), 3.81 (m, 1H), 3.95 (t, 8.2 Hz, 1H), 4.20 (t, 8.2 Hz); $^{13}$C NMR (90 MHz, CDCl$_3$) δ 18.6, 20.0, 25.2, 25.4 (d, $^2J_{CP}$=1.4 Hz), 30.7 (d, $^2J_{CP}$=7.8 Hz), 32.8 (d, J$_{CP}$=47.6 Hz), 32.0, 33.2, 35.1 (d, J$_{CP}$=43.6 Hz), 38.7 (d, J$_{CP}$=39.8 Hz), 70.6, 72.8, 163.7 (d, $^2J_{CP}$=4.5 Hz); $^{31}$P NMR (145 MHz, CDCl$_3$) δ 87.9; ESI MS 288 (M$^+$+H); HRMS calculated for C$_{14}$H$_{27}$NOPS 288.1551 found 288.1545.

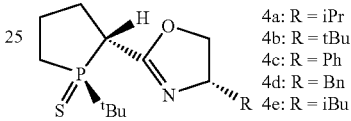

4a: R = iPr
4b: R = tBu
4c: R = Ph
4d: R = Bn
4e: R = iBu

Raney Ni, CH$_3$CN, 80–85%

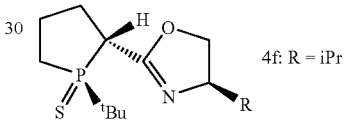

4f: R = iPr

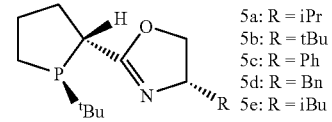

5a: R = iPr
5b: R = tBu
5c: R = Ph
5d: R = Bn
5e: R = iBu

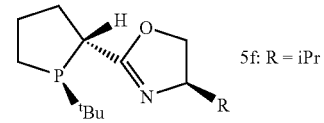

5f: R = iPr

General Procedure

To a N$_2$-flushed Schlenk flask was loaded 5.0 g of Raney Ni 2800 slurry. The Raney Ni was washed sequentially with methanol (10 mL×3), ether (10 mL×3), and dried degassed CH$_3$CN (10 mL×3). To this flask was then transferred a solution of 4a–f (1.5 mmol) in CH$_3$CN (20 mL) via cannula. The resulting mixture was stirred under N$_2$ for 2 d. The mixture was then filtered under N$_2$. The Raney Ni solid was washed with CH$_3$CN (10 mL×5). The combined CH$_3$CN with filtrate was evaporated under N$_2$ to give an oily residue. The residue was passed through an Al$_2$O$_3$ (basic) plug under N$_2$ to give pure oily product 5a–f (80–95%).

5a: $^1$H NMR (400 MHz, CD$_2$Cl$_2$) δ 0.88 (d, 6.8 Hz, 3H), 0.94 (d, 6.8 Hz, 6.8 Hz), 1.08 (d, $^3J_{HP}$=11.9 Hz, 9H), 1.72 (m, 4H), 2.01 (b, 3H), 2.81 (b, 1H), 3.85 (b, 1H), 3.95 (t, 7.6 Hz, 1H), 4.20 (t, 7.6 Hz, 1H); $^{13}$C NMR (100 MHz, CD$_2$Cl$_2$)

δ 18.3, 18.8, 23.3 (d, $^2J_{CP}$=17.5 Hz), 27.6 (d, $^2J_{CP}$=14.5 Hz), 29.0, 29.1 (d, $J_{CP}$=18.4 Hz), 33.2 (d, $J_{CP}$=19.9 Hz), 36.9 (d, $J_{CP}$=20.2 Hz), 70.2, 72.4, 169.1 (d, $^2J_{CP}$=15.9 Hz); $^{31}$P NMR (145 MHz, CD$_2$Cl$_2$) δ 26.0; ESI MS 256 (M$^+$+H); HRMS calculated for C$_{14}$H$_{27}$NOP 256.1830 found 256.1820.

5b: $^1$H NMR (360 MHz, CDCl$_3$) δ 0.71 (s, 9H), 0.90 (d, $^3J_{HP}$=11.9 Hz, 9H), 1.56 (m, 3H), 1.83 (m, 3H), 2.73 (b, 1H), 3.65 (m), 3.92 (t, 7.6 Hz, 1H), 3.99 (t, 9.3 Hz, 1H); $^{13}$C NMR (90 MHz, CDCl$_3$) δ 21.9 (d, $^2J_{CP}$=17.6 Hz), 24.8, 26.4 (d, $^2J_{CP}$=14.2 Hz), 27.7 (d, 2.84 Hz), 28.9 (d, $J_{CP}$=18.0 Hz), 32.4 (d, $J_{CP}$=70.0 Hz), 35.8 (d, $J_{CP}$=19.8 Hz), 67.7, 74.4, 168.9 (d,, $^2J_{CP}$=15.9 Hz); $^{31}$P NMR (145 MHz, CDCl$_3$) δ 25.2; ESI MS 270 (M$^+$+H); HRMS calculated for C$_{15}$H$_{29}$NOP 270.1987 found 270.1972.

5c: $^1$H NMR (360 MHz, CD$_2$Cl$_2$) δ 0.98 (d, $^3J_{HP}$=12.0 Hz, 9H), 1.66 (m, 3H), 1.92 (m, 3H), 2.80 (m, 1H), 3.91 (t, 7.9 Hz, 1H), 4.46 (dd, 8.3 Hz, 10.0 Hz, 1H), 5.01 (m, 1H), 7.17 (m, 5H); $^{13}$C NMR (90 MHz, CD$_2$Cl$_2$) δ 23.5 (d, $^2J_{CP}$=17.6 Hz), 27.9 (d, $^2J_{CP}$=14.4 Hz), 29.2 (d, $^2J_{CP}$=2.1 Hz), 29.4 (d, $J_{CP}$=18.7 Hz), 33.4, 37.1 (d, $J_{CP}$=20.1 Hz), 70.1, 75.3, 127.0–129.1 (m), 144.0, 172.0 (d, $^2J_{CP}$=15.8 Hz); $^{31}$P NMR (145 MHz, CD$_2$Cl$_2$) δ 27.4; ESI MS 290 (M$^+$+H); HRMS calculated for C$_{17}$H$_{24}$NOP 290.1674 found 290.1663.

5d: $^1$H NMR (360 MHz, CD$_2$Cl$_2$) δ 1.06 (d, $^3J_{HP}$=11.9 Hz, 9H), 1.74 (m, 3H), 2.01 (m, 3H), 2.67 (dd, 7.5 Hz, 13.6 Hz, 1H), 2.74 (m, 1H), 2.96 (dd, 6.1 Hz, 13.6 Hz, 1H), 3.92 (dd, 7.0 Hz, 8.2 Hz, 1H), 4.17 (t, 9.0 Hz, 1H), 4.30 (m, 1H), 7.28 (m, 5H); $^{13}$C NMR (90 MHz, CD$_2$Cl$_2$) δ23.4 (d, $J_{CP}$=17.9 Hz), 27.8 (d, $^2J_{CP}$=14.4 Hz), 29.1 (d, $^2J_{CP}$=2.2 Hz), 29.3 (d, $J_{CP}$=18.7 Hz), 33.4 (d, $^2J_{CP}$=1.2 Hz), 37.1 (d, $J_{CP}$=20.0 Hz), 42.5, 68.0, 72.2, 126.8, 128.9, 130.0, 139.2, 170.9 (d, $^2J_{CP}$=15.8 Hz); $^{31}$P NMR (145 MHz, CD$_2$Cl$_2$) δ 26.7; ESI MS 304 (M$^+$+H); HRMS calculated for C$_{18}$H$_{27}$NOP 304.1830 found 304.1836.

5e: $^1$H NMR (360 MHz, CD$_2$Cl$_2$) δ 0.86 (d, 4.3 Hz, 3H), 0.92 (d, 4.3 Hz, 3H), 1.03 (d, $^3J_{HP}$=11.9 Hz, 9H), 1.25 (m, 1H), 1.49 (m, 1H), 1.73 (m, 4H), 1.95 (m, 3H), 2.74 (m, 1H), 3.75 (t, 7.7 Hz, 1H), 4.03 (m, 1H), 4.25 (dd, 8.0 Hz, 9.1 Hz, 1H); $^{13}$C NMR (90 MHz, CD$_2$Cl$_2$) δ23.1, 23.3 (d, $^2J_{CP}$=17.7 Hz), 26.0, 27.8 (d, $^2J_{CP}$=14.4 Hz), 29.1 (d, $^2J_{CP}$=2.4 Hz), 29.2 (d $J_{CP}$=18.7 Hz), 33.3 (d, 1.6 Hz), 37.1 (d, $J_{CP}$=19.9 Hz), 46.3, 65.2, 73.4, 169.9 (d, $^2J_{CP}$=15.8 Hz); $^{31}$P NMR (145 MHz, CD$_2$Cl$_2$) δ26.1; ESI MS 270 (M$^+$+H); HRMS calculated for C$_{15}$H$_{28}$NOP 270.1987 found 270.2042.

5f: $^1$H NMR (360 MHz, CDCl$_3$) δ 0.73 (d, 6.8 Hz, 3H), 0.80 (d, 6.8 Hz, 3H), 0.93 (d, $^3J_{HP}$=12.0 Hz, 9H), 1.49 (m, 1H), 1.66 (m, 3H), 1.89 (m, 3H), 2.66 (m, 1H), 3.76 (m, 1H), 3.84 (t, 7.6 Hz, 1H), 4.07 (t, 8.8 Hz, 1H); $^{13}$C NMR (90 MHz, CDCl$_3$) δ 16.6, 17.9, 21.8 (d, $^2J_{CP}$=17.4 Hz), 26.5 (d, $^2J_{CP}$=14.3 Hz), 27.5 (d, $^2J_{CP}$=2.4 Hz), 27.8 (d, $J_{CP}$=18.0 Hz), 31.3, 31.9 (d, 1.1 Hz), 35.5 (d, $J_{CP}$=19.8 Hz), 68.5, 70.6, 169.0 (d, $^2J_{CP}$=15.5 Hz); $^{31}$P NMR (145 MHz, CDCl$_3$) δ 25.9; ESI MS 256 (M$^+$+H); HRMS calculated for C$_{14}$H$_{27}$NOP 256.1830 found 256.1805.

EXAMPLE 9

Preparation of Ir—PN Compounds

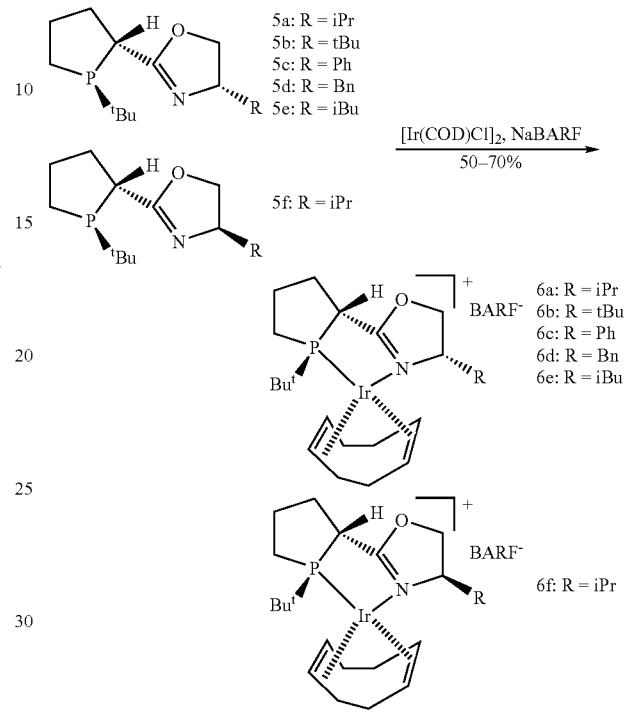

General Procedure

To a Schlenk tube was added 5a–f (0.346 mmol), [Ir(COD)Cl]$_2$ (116 mg, 0.173 mmol), and dried degassed CH$_2$Cl$_2$ (4 mL). The deep red mixture was heated under N$_2$ to reflux for 1 h, until in situ $^{31}$P NMR indicated that the starting material was consumed. After the reaction mixture was cooled to rt, Na[BARF] (453 mg, 0.519 mmol) was added followed by degassed H$_2$O (5 mL), and the resulting two-phase mixture was stirred vigorously for 30 min. The two layers were separated, and the water layer was further washed with CH$_2$Cl$_2$. The combined CH$_2$Cl$_2$ solution was evaporated to give a brown residue, which was subsequently passed through an Al$_2$O$_3$ plug (eluent: hexane: CH$_2$Cl$_2$=1:2) to give pure orange product 6a–f in 50–70% yield.

6a: $^1$H NMR (360 MHz, CD$_2$Cl$_2$) δ 0.74 (d, 6.8 Hz, 3H), 0.91 (d, 7.0 Hz, 3H), 1.17 (d, $^3J_{HP}$=15.4 Hz, 9H), 1.58 (m, 2H), 1.83–2.40 (m, 13H), 3.09 (m, 1H), 4.13 (m, 3H), 4.51 (t, 9.4 Hz, 1H), 4.65 (dd, 3.8 Hz, 9.4 Hz, 1H), 4.94 (m, 2H), 7.59 (s, 4H), 7.73 (s, 8H); $^{13}$C NMR (90 MHz, CD$_2$Cl$_2$) δ 14.0, 19.0, 24.0 (d, $^2J_{CP}$=25.6 Hz), 27.1 (d, $^2J_{CP}$=3.5Hz), 27.8, 30.1 (d, 1.9 Hz), 31.1, 32.2 (d, 1.9 Hz), 32.5 (d, $J_{CP}$=23.4 Hz), 33.9 (d, 2.1 Hz), 36.2 (d, 3.7 Hz), 37.8 (d, $J_{CP}$=30.0 Hz), 60.6, 63.1, 70.0, 73.0, 90.3 (d, 11.8 Hz), 93.5 (d, 10.9 Hz), 118.0 (t), 120.7, 123.7, 126.7, 129.3 (dd, 28.4 Hz, 58.6 Hz), 135.4 (t, 92.9 Hz), 162.3 (q, 49.6 Hz), 190.1 (d, $^2J_{CP}$=19.7 Hz); $^{31}$P NMR (145 MHz, CD$_2$Cl$_2$) δ51.9; ESI+MS: 556 (cation+1); ESI-MS: 863 (anion); HRMS calculated for IrC$_{22}$H$_{39}$NOP 556.2320 found 556.2318; HRMS calculated for C$_{32}$H$_{12}$F$_{24}$B 863.0649 found 863.0650.

6b: $^1$H NMR (360 MHz, CD$_2$Cl$_2$) δ 0.88 (s, 9H), 1.15 (d, $^3$J$_{HP}$=15.4 Hz, 9H), 1.43 (b, 2H), 1.60–2.40 (m, 11H), 2.87 (d, 7.6 Hz, 1H), 3.55 (m, 1H), 3.80 (b, 1H), 4.38 (m, 2H), 4.54 (m, 1H), 4.73 (dd, 1.8 Hz, 9.8 Hz), 5.02 (b, 1H), 7.48 (s, 4H), 7.64 (s, 8H); $^{13}$C NMR (90 MHz, CD$_2$Cl$_2$) δ23.7, 24.0, 25.5, 26.0, 25.5, 27.3 (d, $^2$J$_{CP}$=3.4 Hz), 29.4, 31.5 (d, J$_{CP}$=25.5 Hz), 34.0, 34.8, 35.7, 37.2 (d, J$_{CP}$=30.3 Hz), 37.7, 56.5, 65.2, 71.1, 75.2, 86.0 (d, 16.5 Hz), 96.0 (d, 8.1 Hz), 111.8 (t), 120.7, 123.7, 126.7, 129.4 (dd, 28.5 Hz, 62.7 Hz), 135.4 (t), 162.3 (q, 49.4 Hz), 188.4 (d, $^2$J$_{CP}$=17.9 Hz); $^{31}$P NMR (145 MHz, CD$_2$Cl$_2$) δ 42.4; ESI+MS: 570 (cation+1); HRMS calculated for IrC$_{23}$H$_{41}$NOP 570.2477 found 570.2437; HRMS calculated for C$_{32}$H$_{12}$F$_{24}$B 863.0649 found 863.0633.

6c: $^1$H NMR (360 MHz, CD$_2$Cl$_2$) δ 1.09 (d, $^3$J$_{HP}$=15.5 Hz, 9H), 1.25 (m, 1H), 1.46 (m, 2H), 1.80–2.40 (m, 11H), 3.19 (m, 1H), 3.78 (m, 2H), 4.00 (m, 1H), 4.46 (dd, 5.2 Hz, 9.2 Hz, 1H), 4.81 (m, 1H), 4.93 (dd, 9.4 Hz, 10.0 Hz, 1H), 5.23 (m, 1H), 7.01 (m, 2H), 7.34 (m, 3H), 7.48 (s, 4H) 6.65 (s, 8H); $^{13}$C NMR (100 MHz, CD$_2$Cl$_2$) δ 23.1 (d, $^2$J$_{CP}$=26.5 Hz), 27.3, 27.6, 28.0, 28.5, 30.9, 31.4, 33.0 (d, J$_{CP}$=23.6 Hz), 33.9, 35.4, 37.1 (d, J$_{CP}$=29.9 Hz), 61.7, 62.6, 69.4, 81.3, 93.3 (d, 11.6 Hz), 94.2 (d, 13.9 Hz), 118.3, 121.3, 124.0, 126.5, 126.7, 129.6 (dd, 25.2 Hz, 67.1 Hz), 130.5 (m), 135.6, 139.2, 162.5 (q, 49.5 Hz), 191.3 (d, $^2$J$_{CP}$=19.8 Hz); $^{31}$P NMR (145 MHz, CD$_2$Cl$_2$) δ 53.7; ESI+MS: 590 (cation+1); HRMS calculated for IrC$_{25}$H37NOP 590.2164 found 570.2120.

6d: $^1$H NMR (360 MHz, CD$_2$Cl$_2$) δ 1.18 (d, $^3$J$_{HP}$=15.5 Hz, 9H), 1.64 (m, 3H), 1.80–2.50 (m, 11H), 2.61 (dd, 9.8 Hz, 14.1 Hz, 1H), 3.06 (m, 2H), 4.08 (m, 1H), 4.29 (m, 2H), 4.49 (t, 9.0 Hz, 1H), 4.69 (dd, 2.7 Hz, 9.4 Hz), 4.98 (m, 1H), 5.12 (b, 1H), 7.20 (m, 2H), 7.35 (m, 3H), 7.57 (s, 4H), 7.73 (s, 8H); $^{13}$C NMR (100 MHz, CD$_2$Cl$_2$) δ 23.7 (d, $^2$J$_{CP}$=24.6 Hz), 26.6, 27.0 (d, $^2$J$_{CP}$=3.7 Hz), 27.2, 30.0 (d, J$_{CP}$=15.4 Hz), 32.1, 32.3 (d, 6.3 Hz), 33.4, 36.3 (d, 3.7 Hz), 36.7 (d, J$_{CP}$=30.1 Hz), 41.4, 60.4, 64.0, 65.2, 76.6, 88.9 (d, 12.6 Hz), 94.3 (d, 10.3 Hz), 117.8, 120.9, 123.6, 126.3, 128.3, 129.1 (m), 129.6, 134.5, 135.2, 162.0 (q, 49.5 Hz), 190.1 (d, $^2$J$_{CP}$=19.2 Hz); $^{31}$P NMR (145 MHz, CD$_2$Cl$_2$) δ 52.0; ESI+MS: 604 (cation+1); HRMS calculated for IrC$_{26}$H39NOP 604.2320 found 604.2322.

6e: $^1$H NMR (360 MHz, CD$_2$Cl$_2$) δ 0.93 (d, 6.5 Hz, 3H), 0.97 (d, 6.5 Hz), 1.18 (d, $^3$J$_{HP}$=15.5 Hz, 9H), 1.39 (m, 2H), 1.60 (m, 4H), 1.80–2.50 (m, 11H), 3.06 (d, 7.6 Hz), 3.98 (m, 2H), 4.21 (m, 1H), 4.56 (m, 2H), 4.77 (m, 1H), 5.01 (m, 1H), 7.57 (s, 4H), 7.73 (s, 8H); $^{13}$C NMR (90 MHz, CD$_2$Cl$_2$) δ 21.6, 23.8, 23.9 (d, $^2$J$_{CP}$=24.6 Hz), 25.8, 26.5, 27.1 (d, $^2$J$_{CP}$=3.7 Hz), 27.4, 30.2, 32.3 (d, J$_{CP}$=24.1 Hz), 32.5, 33.8, 36.4 (d, 3.8 Hz), 37.0 (d, J$_{CP}$=30.2 Hz), 45.0, 60.4, 63.3, 64.0, 77.6, 89.2 (d, 12.4 Hz), 64.6 (d, 40.9 Hz), 118.1 (t), 120.7, 123.7, 126.7, 129.5 (dd, 37.7 Hz, 76.2 Hz), 135.4 (t, 103.7 Hz), 162.4 (q, 49.7 Hz), 189,5 (d, $^2$J$_{CP}$=24.6 Hz); $^{31}$P NMR (145 MHz, CD$_2$Cl$_2$) δ 51.3; ESI+MS: 570 (cation+1); HRMS calculated for IrC$_{23}$H$_{41}$NOP 570.2477 found 570.2423.

6f: $^1$H NMR (400 MHz, CD$_2$Cl$_2$) δ 0.79 (d, 6.8 Hz, 3H), 1.00 (d, 7.1 Hz, 3H), 1.18 (d, $^3$J$_{HP}$=15.5 Hz, 9H), 1.80–2.30 (m, 12H), 2.40 (m, 2H), 3.55 (m, 1H), 4.18 (m, 1H), 3.93 (m, 1H), 4.46 (m, 1H), 4.52 (t, 9.4 Hz, 1H), 4.58 (m, 1H), 4.75 (dd, 3.6 Hz, 9.7 Hz, 1H), 5.02 (m, 1H), 7.61 (s, 4H), 7.77 (s, 8H); $^{13}$C NMR (100 MHz, CD$_2$Cl$_2$) δ 14.3 (d, 9.6 Hz), 18.6 (d, 3.5 Hz), 22.6 (d, $^2$J$_{CP}$=29.7 Hz), 27.1 (d, $^2$J$_{CP}$=4.6 Hz), 27.6, 27.7, 31.5, 31.8, 32.5, 33.5 (d, J$_{CP}$=21.2 Hz), 35.1, 36.4 (d, J$_{CP}$=30.4 Hz), 62.5 (d, 7.5 Hz), 65.4, 68.9, 73.3, 85.6 (d, 14.2 Hz), 94.9 (d, 8.7 Hz), 117.7, 120.9, 123.6, 126.3, 129.2 (dd, 37.2 Hz, 68.5 Hz), 135.2, 162.1 (q, 49.7 Hz), 187.0 (d, $^2$J$_{CP}$=20.9 Hz); $^{31}$P NMR (145 MHz, CD$_2$Cl$_2$) δ 60.0; ESI+MS: 556 (cation+1); ESI-MS: 863 (anion); HRMS calculated for IrC$_{22}$H$_{39}$NOP 556.2320 found 556.2309; HRMS calculated for C$_{32}$H$_{12}$F$_{24}$B 863.0649 found 863.0650.

EXAMPLE 10

Asymmetric Reduction of Unfunctionalized Alkenes General Hydrogenation Procedure To a solution of an olefin substrate (0.2 mmol) in CH$_2$Cl$_2$ (2 mL) was added Ir complex 6 (2 μmol, 1 mol %) under nitrogen. The solution was then transferred into an autoclave. The hydrogenation was performed at room temperature under 50 bar of H$_2$ for 12–48 h. After carefully releasing the hydrogen, the reaction mixture was evaporated. The residue was re-dissolved with ethyl acetate, which was subsequently passed through a short silica gel plug to remove the catalyst.

The resulting solution was directly used for chiral GC or HPLC to measure the enantiomeric excess.

Ir-catalyzed Asymmetric Hydrogenation of Methylstilbenes

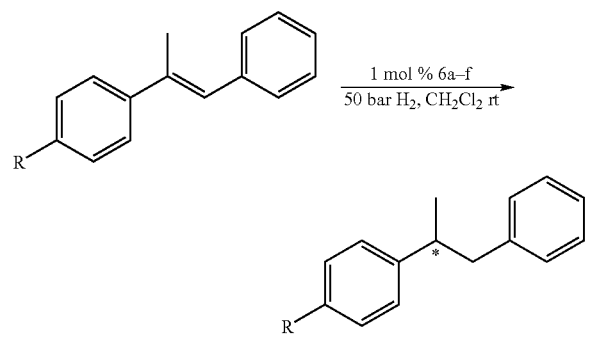

| Entry[a] | Substrate | R | Catalyst | ee %[b] | Config.[c] |
|---|---|---|---|---|---|
| 1 | | H | 6a | 91 | R |
| 2 | | H | 6b | 81 | R |
| 3 | | H | 6c | 95 | R |
| 4 | | H | 6d | 89 | R |
| 5 | | H | 6e | 75 | R |
| 6 | | H | 6f | 77 | S |
| 7 | | OMe | 6c | 91 | R |
| 8 | | Cl | 6c | 90 | R |

[a]See Experimental Section for detailed conditions.
[b]ee's were determined by Chiral HPLC (Chiralcel OJH).
[c]The absolute configuration was assigned by comparison of optical rotation with reported data.

Ir-catalyzed Asymmetric Hydrogenation of
β-methylcinnamic Esters $$\text{Ar}\underset{}{\overset{}{\diagup\hspace{-6pt}=\hspace{-6pt}\diagdown}}\text{COOMe} \xrightarrow[50 \text{ bar } H_2, CH_2Cl_2 \text{ rt}]{1 \text{ mol } \% \text{ 6a–f}} \text{Ar}\overset{*}{\diagup}\text{COOMe}$$

| Entry[a] | Substrate | R | Catalyst | ee %[b] | Config.[c] |
|---|---|---|---|---|---|
| 1 | 7 | Ph | 6a | 94 | R |
| 2 | 7 | Ph | 6b | 91 | R |
| 3 | 7 | Ph | 6c | 98 | R |
| 4 | 7 | Ph | 6d | 92 | R |
| 5 | 7 | Ph | 6e | 95 | R |
| 6 | 7 | Ph | 6f | 93 | S |
| 7 | 8 | p-F—Ph | 6c | 95 | R |
| 8 | 9 | p-Cl—Ph | 6c | 98 | R |
| 9 | 10 | p-CH$_3$—Ph | 6c | 97 | R |
| 10 | 11 | p-OCF$_3$—Ph | 6c | 97 | R |
| 11 | 12 | p-OCH$_3$—Ph | 6c | 97 | R |
| 12 | 13 | m-CH$_3$—Ph | 6c | 99 | R |
| 13 | 14 | 1-naphthyl | 6c | 98 | R |
| 14 | 15 | 2-naphthyl | 6c | 95 | R |
| 15 | (Z)-9 | p-Cl—Ph | 6c | 80 | S |

[a]See Experimetal Section for detailed conditions.
[b]ee's were determined by chiral HPLC (Chiralcel OJH) or Chiral GC (Chiralselect 1000).
[c]The absolute configuration was assigned by comparison of optical rotation with reported data or by analogy.

A series of (E)-α,β-unsaturated esters were prepared via a Heck reaction according to a known procedure: Littke, A. F.; Fu, G. C. *J. Am. Chem. Soc.*, 2001, 123, 6989–7000. To a Schlenk flask was added aryl halide (6.6 mmol), methyl crotonate (1.40 mL, 13.2 mmol), Pd$_2$(dba)$_2$ (151 mg, 165 μmol), Cy$_2$NMe (1.55 mL, 7.26 mmol), degassed dried dioxane (20 mL), and then $^t$Bu$_3$P (67 mg, 0.33 mmol). The whole mixture was stirred under N$_2$ at rt overnight. At the conclusion of the reaction, the mixture was diluted with Et$_2$O, filtered through a pad of silica gel with copious washing, concentrated, and purified through column chromatography to give product in 70–80% yield.

7: $^1$H NMR (300 MHz, CDCl$_3$) δ 2.62 (d, 1.3 Hz, 3H), 3.78 (s, 3H), 6.17 (d, 1.2 Hz, 1H), 7.40 (m, 3H), 7.51 (m, 2H); $^{13}$C NMR (90 MHz, CDCl$_3$) δ 18.4, 51.5, 117.1, 126.7, 128.9, 129.5, 142.6, 156.3, 167.7; APCI MS: 177 (M$^+$+1); HRMS calculated for C$_{11}$H$_{13}$O$_2$ 177.0916 found 177.0906.

8: $^1$H NMR (360 MHz, CDCl$_3$) δ 2.55 (d, 1.2 Hz, 3H), 3.74 (s, 3H), 6.09 (d, 1.2 Hz, 1H), 7.05 (m, 2H), 7.45 (m, 2H); $^{13}$C NMR (90 MHz, CDCl$_3$) δ 18.2, 51.3, 115.6 (d, 21.6 Hz), 116.8, 128.8 (d, 32.0 Hz), 138.4, 154.7, 162.1, 164.8, 167.3; APCI MS: 195 (M$^+$+1); HRMS calculated for C$_{11}$H$_{12}$O$_2$F 195.0821 found 195.0824.

9: $^1$H NMR (300 MHz, CDCl$_3$) δ 2.58 (d, 1.3 Hz, 3H), 3.78 (s, 3H), 6.14 (dd, 1.2 Hz, 2.4 Hz, 1H), 7.38 (m, 4H); $^{13}$C NMR (75 MHz, CDCl$_3$) δ 18.3, 51.6, 117.5, 128.0, 129.1, 135.5, 140.9, 154.8, 167.5; APCI MS: 211 (M$^+$+1); HRMS calculated for C$_{11}$H$_{12}$O$_2$Cl 211.0526 found 211.0519.

10: $^1$H NMR (300 MHz, CDCl$_3$) δ 2.40 (s, 3H), 2.61 (d, 1.2 Hz, 3H), 3.79 (s, 3H), 6.17 (d, 1.2 Hz, 1H), 7.21 (d, 8.0 Hz, 2H), 7.42 (d, 8.0 Hz, 2H); $^{13}$C NMR (75 MHz, CDCl$_3$) δ18.3, 21.6, 51.5, 116.2, 126.7, 129.6, 139.6, 156.2, 167.8; APCI MS: 191 (M$^{30}$ +1); HRMS calculated for C$_{12}$H$_{15}$O$_2$ 191.1072 found 191.1058.

11: $^1$H NMR (360 MHz, CDCl$_3$) δ 2.59 (d, 1.2 Hz, 3H), 3.79 (s, 3H), 6.15 (d, 1.2 Hz, 1H), 7.24 (d, 8.1 Hz, 2H), 2.55 (dd, 2.0 Hz, 7.9 Hz); $^{13}$C NMR (90 MHz, CDCl$_3$) δ 18.1, 51.3, 117.7, 119.2, 121.0, 121.1, 128.0, 140.9, 149.9, 154.3, 167.1;

12: $^1$H NMR (300 MHz, CDCl$_3$) δ 2.58 (d, 1.2 Hz, 3H), 3.74 (s, 3H), 3.81 (s, 3H), 6.13 (dd, 1.1 Hz, 2.4 Hz, 1H), 6.89 (dd, 2.1 Hz, 6.8 Hz, 2H), 7.45 (dd, 2.1 Hz, 6.8 Hz, 2H); $^{13}$C NMR (75 MHz, CDCl$_3$) δ 18.0, 51.4, 55.7, 114.2, 115.2, 134.5, 155.6, 160.9, 167.8; APCI MS: 207 (M$^{30}$ +1); HRMS calculated for C$_{12}$H$_{15}$O$_3$ 207.1021 found 207.1023.

13: $^1$H NMR (360 MHz, CDCl$_3$) δ 2.40 (s, 3H), 2.60 (d, 1.0 Hz, 3H), 3.78 (s, 3H), 6.16 (d, 1.0 Hz, 1H), 7.21 (m, 1H), 7.29 (m, 3H); $^{13}$C NMR (90 MHz, CDCl$_3$) δ 18.2, 21.6, 51.2, 116.8, 123.6, 127.2, 128.6, 130.0, 138.3, 142.4, 156.3, 167.5; ESI MS: 191 (M$^{30}$ +1); HRMS calculated for C$_{12}$H$_{15}$O$_2$ 191.1072 found 191.1091.

14: $^1$H NMR (360 MHz, CDCl$_3$) δ 2.68 (s, 3H), 3.83 (s, 3H), 6.04 (s, 1H), 7.32 (m, 1H), 7.53 (m, 3H), 7.90 (m, 3H); $^{13}$C NMR (90 MHz, CDCl$_3$) δ 21.9, 51.3, 120.4, 124.4, 125.4, 126.2, 126.5, 128.4, 128.7, 130.3, 133.9, 142.2, 157.6, 167.2; ESI MS: 227 (M$^{30}$ +1); HRMS calculated for C$_{15}$H$_{15}$O$_2$ 227.1072 found 227.1066.

15: $^1$H NMR (300 MHz, CDCl$_3$) δ 2.74 (s, 3H), 3.82 (s, 3H), 6.33 (s, 1H), 7.56 (m, 3H), 7.90 (m, 4H); $^{13}$C NMR (75 MHz, CDCl$_3$) δ 18.4, 51.6; 117.5, 124.4, 126.4, 127.0, 127.2, 128.0, 128.6, 128.9, 133.5, 133.9, 139.6, 156.1, 167.7; APCI MS: 227 (M$^{30}$ +1); HRMS calculated for C$_{15}$H$_{15}$O$_2$ 227.1072 found 227.1064.

Analytical Data and GC or HPLC Conditions for New Hydrogenation Products

Hydrogenation Product of 7:

98% ee; [α]$^{20}_D$=-15.5° (c=0.7, CHCl$_3$); chiral HPLC: Chiralcel OJH, hex: iPr=95:5, t$_R$=7.9 min (R), 9.0 min (S); $^1$H NMR (300 MHz, CDCl$_3$) δ 1.33 (d, 7.0 Hz, 3H), 2.58 (dd, 8.2 Hz, 15.1 Hz, 1H), 2.66 (dd, 6.9 Hz, 15.1 Hz, 1H), 3.30 (s, 3H), 7.31 (m, 5H); $^{13}$C NMR (75 MHz, CDCl$_3$) δ 22.2, 36.9, 43.2, 51.9, 126.8, 127.1, 128.9, 146.1, 173.3; APCI MS: 196 (M$^+$+NH$_4^+$); HRMS calculated for C$_{11}$H$_{18}$NO$_2$ 196.1338 found 196.1335.

Hydrogenation Product of 8

95% ee; [α]$^{20}_D$=-1.9° (c=0.5, CHCl$_3$); chiral GC: Chiralselect 1000, 140° C., t$_R$=19.3 min (S), 19.9 min (R); $^1$H NMR (400 MHz, CDCl$_3$) δ 1.31 (d, 7.0 Hz, 3H), 2.60 (m, 2H), 3.30 (m, 1H), 3.64 (s, 3H), 7.16 (d, 8.0 Hz, 2H), 7.27 (m, 2H); $^{13}$C NMR (100 MHz, CDCl$_3$) δ 22.2, 36.2, 43.0, 51.9, 121.4, 128.4, 144.7, 148.1, 172.9; APCI MS: 214 (M$^+$+NH$_4^+$); HRMS calculated for C$_{11}$H$_{17}$FNO$_2$ 214.1243 found 214.1248.

Hydrogenation Product of 9

98% ee; [α]$^{20}_D$=-32.4° (c=1.1, CHCl$_3$); chiral GC: Chiralselect 1000, 140° C., t$_R$=53.7 min (S), 55.5 min (R); $^1$H NMR (300 MHz, CDCl$_3$) δ 1.29 (d, 7.0 Hz, 3H), 2.58 (m, 2H), 3.29 (m, 1H), 3.63 (s, 3H), 7.17 (m, 2H), 7.27 (m, 2H); $^{13}$C NMR (75 MHz, CDCl$_3$) δ 22.2, 36.3, 43.0, 52.0, 128.5, 129.0, 132.4, 144.5, 173.0; APCI MS: 230 (M$^+$+NH$_4^+$); HRMS calculated for C$_{11}$H$_{17}$ClNO$_2$ 230.0948 found 230.0942.

Hydorgenation Product of 10

97% ee; $[\alpha]^{20}{}_D=-2.4°$ (c=0.3, CHCl$_3$); chiral GC: Chiralselect 1000, 140° C., $t_R$=27.1 min (S), 27.7 min (R); $^1$H NMR (400 MHz, CDCl$_3$) δ 1.31 (d, 7.0 Hz, 3H), 2.35 (s,3H), 2.56 (dd, 8.2 Hz, 15.1 Hz, 1H), 2.64 (dd, 7.0 Hz, 15.1 Hz, 1H), 3.29 (m, 1H), 3.66 (s, 3H), 7.14 (s, 4H); $^{13}$C NMR (100 MHz, CDCl$_3$) δ 21.4, 22.3, 36.4, 43.2, 51.9, 127.0, 129.6, 136.3, 143.1, 173.3; ESI MS: 210 (M$^+$+NH$_4{}^+$); HRMS calculated for C$_{12}$H$_{20}$NO$_2$ 210.1494 found 210.1479.

Hydrogenation Product of 11

97% ee; $[\alpha]^{20}{}_D=-23.4°$ (c=0.3, CHCl$_3$); chiral GC: Chiralselect 1000, 140° C., $t_R$=20.0 min (S), 20.5 min (R); $^1$H NMR (400 MHz, CDCl$_3$) δ 1.30 (d, 7.0 Hz, 3H), 2.58 (m, 2H), 3.29 (m, 1H), 3.66 (s, 3H), 6.99 (m, 2H), 7.20 (m, 2H); $^{13}$C NMR (100 MHz, CDCl$_3$) δ 22.4, 36.2, 43.2, 51.9, 115.5, 128.5, 141.7, 160.6, 163.1, 173.1; ESI MS: 280 (M$^+$+NH$_4{}^+$); HRMS calculated for C$_{12}$H$_{17}$F$_3$NO$_3$ 280.1161 found 280.1173.

Hydrogenation Product of 12

97% ee; $[\alpha]^{20}{}_D=-23.8°$ (c=0.7, CHCl$_3$); chiral HPLC: Chiralcel OJH, hex: iPr=95: 5, $t_R$=12.1 min (R), 13.9 min (S); $^1$H NMR (360 MHz, CDCl$_3$) δ 1.27 (d, 7.5 Hz, 3H), 2.52 (dd, 8.0 Hz, 15.0 Hz, 1H), 2.59 (dd, 7.1 Hz, 15.0 Hz, 1H), 3.61 (s, 3H), 3.78 (s, 3H), 6.83 (m, 2H), 7.15 (m, 2H); $^{13}$C NMR (90 MHz, CDCl$_3$) δ 22.1, 35.9, 43.2, 51.6, 55.4, 114.1, 127.8, 138.1, 158.3, 173.1; ESI MS: 226 (M$^+$+NH$_4{}^+$); HRMS calculated for C$_{12}$H$_{20}$NO$_3$ 226.1443 found 226.1425.

Hydrogenation Product of 13

99% ee; $[\alpha]^{20}{}_D=-20.2°$ (c=0.5, CHCl$_3$); chiral GC: Chiralselect 1000, 140° C., $t_R$=47.0 min (S), 48.0 min (R); $^1$H NMR (360 MHz, CDCl$_3$) δ 1.31 (d, 7.0 Hz, 3H), 2.35 (s, 3H), 2.52 (dd, 8.4 Hz, 15.2 Hz, 1H), 2.64 (dd, 6.7 Hz, 15.1 Hz, 1H), 3.25 (m, 1H), 3.65 (s, 3H), 7.04 (m, 3H), 7.21 (m, 1H); $^{13}$C NMR (90 MHz, CDCl$_3$) δ 21.6, 22.0, 35.5, 36.5, 42.9, 51.6, 123.9, 127.4, 127.7, 128.6, 138.2, 145.9, 173.1; ESI MS: 210 (M$^+$+NH$_4{}^+$); HRMS calculated for C$_{12}$H$_{20}$NO$_2$ 210.1494 found 210.1479.

Hydrogenation Product of 14

98% ee; $[\alpha]^{20}{}_D=+1.8°$ (c=0.72, CHCl$_3$); chiral HPLC: Chiralcel OJH, hex: iPr=99:1, $t_R$=32.2 min (R), 36.5 min (S); $^1$H NMR (400 MHz, CDCl$_3$) δ 1.48 (d, 6.9 Hz, 3H), 2.67 ( dd, 9.3 Hz, 15.3 Hz, 1H), 2.89 (dd, 5.3 Hz, 15.3 Hz, 1H), 3.70 (s, 3H), 4.21 (m, 1H), 7.50 (m, 4H), 7.77 (d, 8.0 Hz, 1H), 7.90 (d, 8.0 Hz, 1H), 8.22 (d, 8.4 Hz, 1H); $^{13}$C NMR (100 MHz, CDCl$_3$) δ 21.6, 31.2, 42.7, 51.9, 122.7, 123.4, 125.9, 126.5, 127.4, 129.4, 131.5, 134.4, 142.1, 173.5; ESI MS: 246 (M$^+$+NH$_4{}^+$); HRMS calculated for C$_{15}$H$_{20}$NO$_2$ 246.1494 found 246.1497.

Hydrogenation Product of 15

95% ee; $[\alpha]^{20}{}_D=-40.2°$ (c=1.2, CHCl$_3$); chiral HPLC: Chiralcel OJH, hex: iPr=99:1, $t_R$=65.2 min (R), 70.9 min (S); $^1$H NMR (300 MHz, CDCl$_3$) δ 1.43 (d, 7.0 Hz, 3H), 2.68 (dd, 8.1 Hz, 15.2 Hz, 1H), 2.78 (dd, 7.0 Hz, 15.2 Hz, 1H), 3.49 (m, 1H), 3.65 (s, 3H), 7.46 (m, 3H), 7.69 (s, 1H), 7.83 (m, 2H); $^{13}$C NMR (75 MHz, CDCl$_3$) δ 22.2, 37.0, 43.1, 52.0, 125.4, 125.8, 125.9, 126.4, 128.0, 128.1, 128.6, 132.8, 134.0, 143.6, 173.3; ESI MS: 246 (M$^+$+NH$_4{}^+$); HRMS calculated for C$_{15}$H$_{20}$NO$_2$ 246.1494 found 246.1481.

EXAMPLE 10

Synthesis and Structure of the following Bisphosphine

Synthesis and application of TangPhos Type Ligands

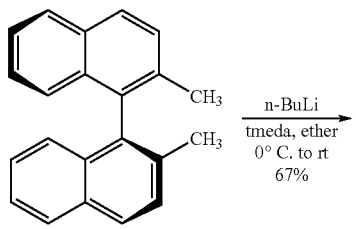

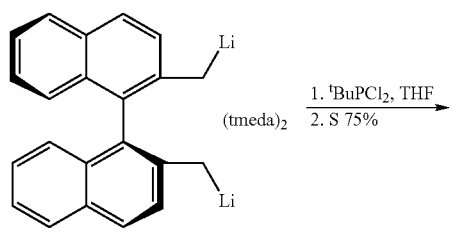

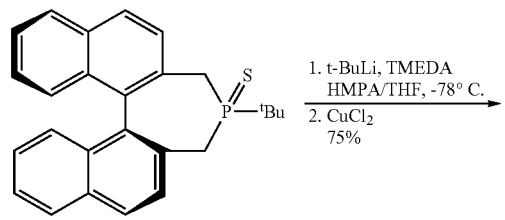

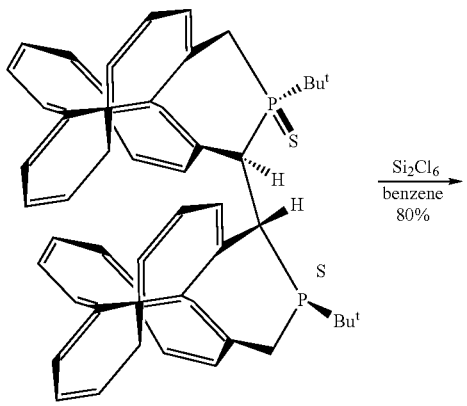

-continued
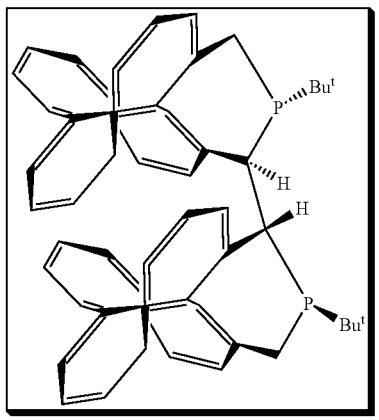
L*
A chiral bisphosphine with the following structure was prepared by the procedure outlined above:
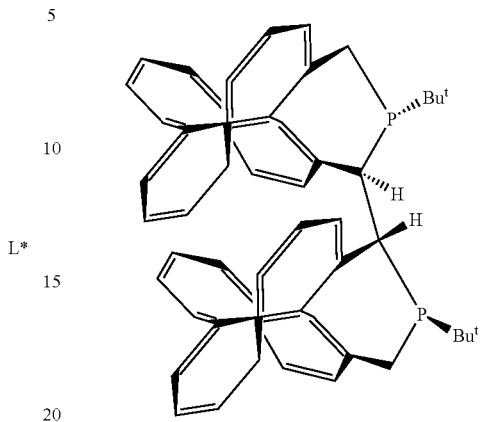
The X-ray structure of the corresponding bisphosphine sulfide was obtained and is shown below:

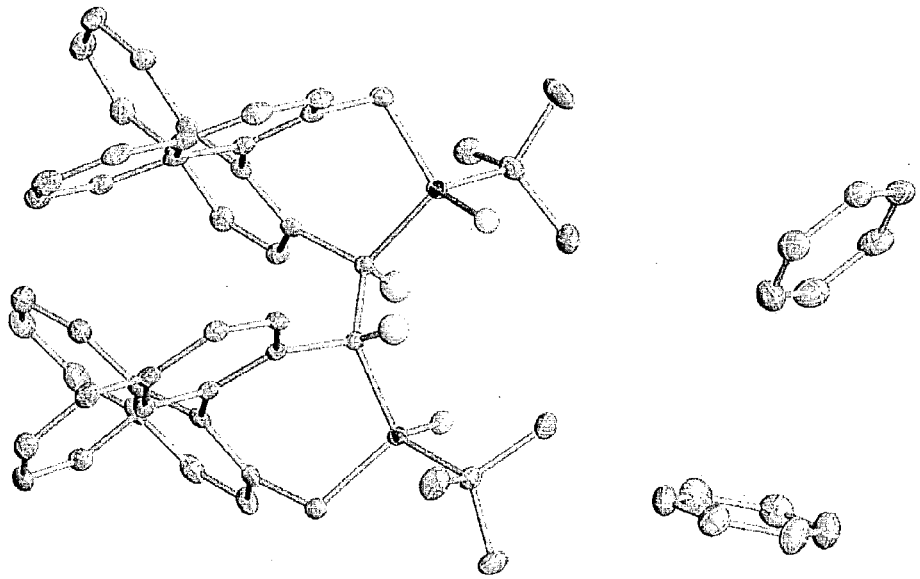
Further Applications
Rh-compound with this ligand is an effective catalyst for hydrogenation of enamides (e.g., E/Z mixture of PhCH(NHAc)CHCOOEt) to make beta amino acids (up to 99% ee has been achieved).

Further Applications

Rh-compound with this ligand is an effective catalyst for hydrogenation of enamides (e.g., E/Z mixture of PhCH(NHAc)CHCOOEt) to make beta amino acids (up to 99% ee has been achieved).

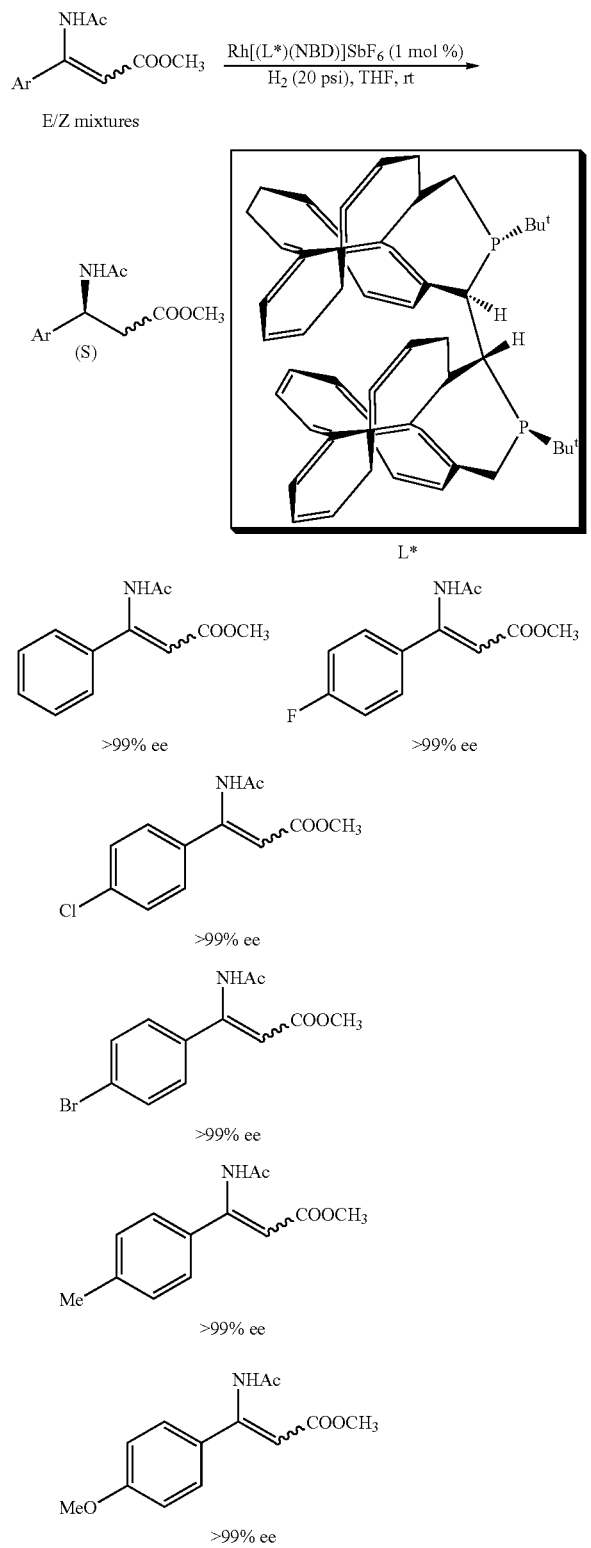

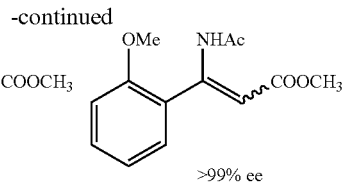

>99% ee  >99% ee

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A chiral ligand represented by the following formula or its enantiomer:

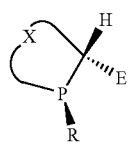

wherein X is a divalent group selected from the group consisting of: $(CR^4R^5)_n$ and $(CR^4R^5)_n$—Z—$(CR^4R^5)_n$, wherein each n is independently an integer from 1 to 6; wherein each $R^4$ and $R^5$ is independently selected from the group consisting of: hydrogen, alkyl, aryl, substituted alkyl, substituted aryl, halogen, hydroxy, alkoxy, aryloxy, alkylthio and amido; and wherein Z is selected from the group consisting of: PR' wherein each R' is independently selected from the group consisting of: hydrogen, alkyl, substituted alkyl, aryl, substituted aryl, hydroxy, alkoxy, aryloxy, acyl and alkoxycarbonyl;

wherein R is selected from the group consisting of: alkyl, aryl, substituted alkyl, substituted aryl, alkoxy and aryloxy;

wherein E is selected from the group consisting of: $PR'_2$, $CH_2PR'_2$, and a group represented by the formula:

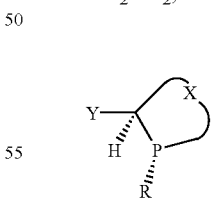

wherein Y is selected from the group consisting of:

$(CR^4R^5)_m$ and $(CR^4R^5)_m$—Z—$(CR^4R^5)_m$;

wherein each m is independently an integer from 0 to 3; wherein each $R^4$ and $R^5$ is independently selected from the group consisting of: hydrogen, alkyl, aryl, substituted alkyl, substituted aryl, halogen, hydroxy, alkoxy, aryloxy, alkylthio, and amido; and wherein Z is selected from the group consisting of: PR' wherein each R' is independently selected from the group consisting of: hydrogen, alkyl, substituted alkyl, aryl, substituted aryl, hydroxy, alkoxy, aryloxy, acyl and alkoxycarbonyl.

2. The chiral ligand of claim 1, wherein:

X is selected from the group consisting of: $(CH_2)_n$ wherein n is from 1 to 6, $CH_2CH(R')CH(R')$, $CH_2CH(OR')CH(OR')$ and $CH_2CH(OH)CH(OH)$.

3. The chiral ligand of claim 1, wherein:

Y is selected from the group consisting of: $(CR^4R^5)_m$ wherein $R^4$ and $R^5$ are hydrogens and wherein m is from 0 to 3, $CH_2PR'CH_2$, $CR'2$, alkylene, and substituted alkylene.

4. A chiral ligand represented by the formula and its enantiomer:

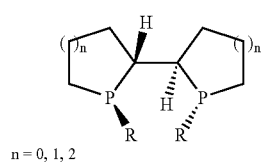

n = 0, 1, 2 wherein R is selected from the group consisting of: alkyl, aryl, substituted alkyl, substituted aryl, alkoxy and aryloxy.

5. The chiral ligand of claim 4, wherein n is 0, 1 or 2, and R is selected from the group consisting of: $CH_3$, Et, iPr, t-Bu, 1-adamantyl, $Et_3C$, cyclo-$C_5H_9$, cyclo-$C_6H_{11}$, phenyl, p-tolyl, 3,5-dimethylphenyl, 3,5-di-t-butyl phenyl, ortho-anisyl and naphthyl.

6. A chiral ligand represented by the formula and its enantiomer:

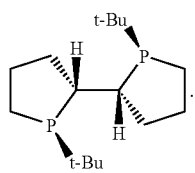

7. A chiral ligand selected from the group consisting of compounds represented by formulas L1 through L5, L7, L8, L22, L24 through L30, L43 through L46, L50 and L51 and their enantiomers:

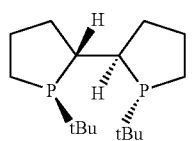
L1

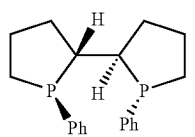
L2

-continued

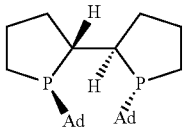
L3

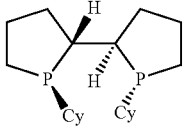
L4

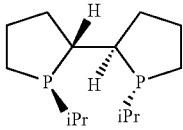
L5

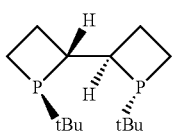
L7

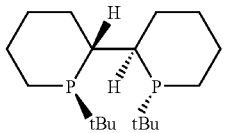
L8

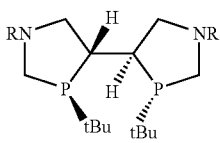
L11

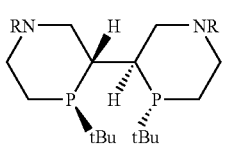
L12

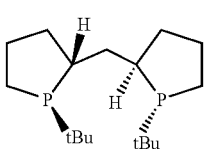
L22

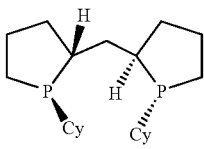
L24

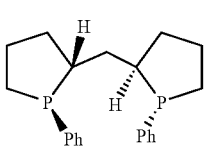
L25

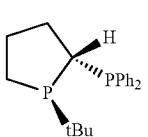
L26

-continued
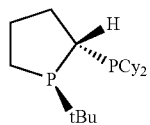 L27
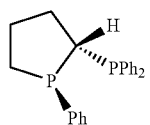 L28
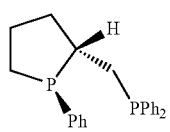 L29
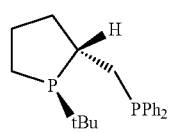 L30
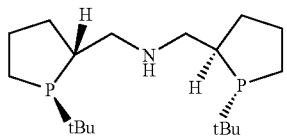 L39
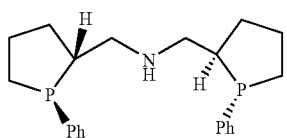 L40
L42
L43
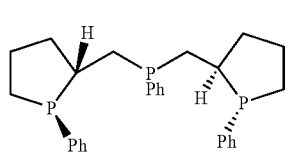
-continued
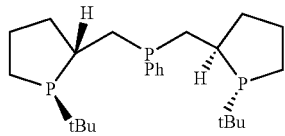 L44
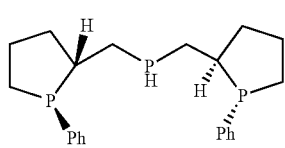 L45
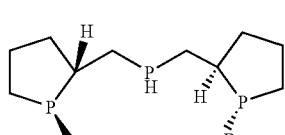 L46
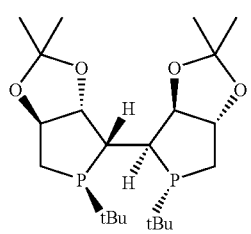 L48
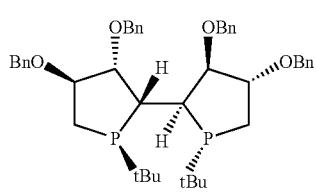 L50
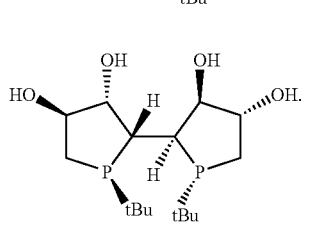 L51
* * * * *